United States Patent
Kobayashi et al.

(10) Patent No.: US 10,138,240 B2
(45) Date of Patent: Nov. 27, 2018

(54) CRYSTAL OF 5-HYDROXY-4-(TRIFLUOROMETHYL) PYRAZOLOPYRIDINE DERIVATIVE

(71) Applicant: Daiichi Sankyo Company, Limited, Chuo-ku, Tokyo (JP)

(72) Inventors: Katsuhiro Kobayashi, Shinagawa-ku (JP); Toshio Kaneko, Shinagawa-ku (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 15/580,450

(22) PCT Filed: Jun. 10, 2016

(86) PCT No.: PCT/JP2016/067307
§ 371 (c)(1),
(2) Date: Dec. 7, 2017

(87) PCT Pub. No.: WO2016/199877
PCT Pub. Date: Dec. 15, 2016

(65) Prior Publication Data
US 2018/0170926 A1    Jun. 21, 2018

(30) Foreign Application Priority Data

Jun. 11, 2015 (JP) .................. 2015-118569

(51) Int. Cl.
| A61P 3/06 | (2006.01) |
| A61P 9/10 | (2006.01) |
| A61K 31/497 | (2006.01) |
| A61K 31/506 | (2006.01) |
| C07D 471/04 | (2006.01) |

(52) U.S. Cl.
CPC .......... *C07D 471/04* (2013.01); *A61K 31/497* (2013.01); *A61K 31/506* (2013.01); *A61P 3/06* (2018.01); *A61P 9/10* (2018.01); *C07B 2200/13* (2013.01)

(58) Field of Classification Search
None
See application file for complete search history.

(56) References Cited

U.S. PATENT DOCUMENTS

| 7,799,782 B2 | 9/2010 | Munson et al. |
| 9,150,575 B2 | 10/2015 | Kobayashi et al. |
| 2013/0165478 A1 | 6/2013 | Schiemann et al. |
| 2015/0152102 A1 | 6/2015 | Kobayashi et al. |

FOREIGN PATENT DOCUMENTS

| EP | 3 081 566 A1 | 10/2016 |
| JP | 2013-536807 A | 9/2013 |
| JP | 2015-113323 A | 6/2015 |
| WO | 2008/002591 A2 | 1/2008 |
| WO | 2012/028243 A1 | 3/2012 |
| WO | 2013/187462 A1 | 12/2013 |
| WO | 2015/087994 A1 | 6/2015 |
| WO | 2015/087995 A1 | 6/2015 |
| WO | 2015/087996 A1 | 6/2015 |
| WO | 2015/111545 A1 | 7/2015 |

OTHER PUBLICATIONS

Badimon, J.J., et al., "Regression of Atherosclerotic Lesions by High Density Lipoprotein Plasma Fraction in the Cholesterol-Fed Rabbit," Journal of Clinical Investigation 85(4):1234-1241, Apr. 1990.
Balicki, R., "Studies in the Field of Nitrogen Heterocyclic Compounds. Part. XI. Abnormal Cyclocondensation of Ethyl 4,4,4-trifluoroacetoacetate With Aminopyrazoles," Polish Journal of Chemistry 57:789-797, 1983.
Extended European Search Report dated Apr. 11, 2017, issued in European Application No. 14869320.3, filed Dec. 12, 2014, 5 pages.
International Preliminary Report on Patentability dated Jun. 14, 2016, issued in corresponding International Application No. PCT/JP2014/082943, filed Dec. 12, 2014, 6 pages.
International Search Report and Written Opinion dated Feb. 17, 2015, issued in corresponding International Application No. PCT/JP2014/082943, filed Dec. 12, 2014, 18 pages.
Iwata, A., et al., "Antiatherogenic Effects of Newly Developed Apolipoprotein A-I Mimetic Peptide/Phospholipid Complexes Against Aortic Plaque Burden in Watanabe-Heritable Hyperlipidemic Rabbits," Atherosclerosis 218(2):300-307, Oct. 2011.
Matsuura, F., et al., "HDL From CETP-Deficient Subjects Shows Enhanced Ability to Promote Cholesterol Efflux from Macrophages in an apoE- and ABCG1-Dependent Pathway," Journal of Clinical Investigation 116(5):1435-1442, May 2006.

(Continued)

*Primary Examiner* — Zinna Northington Davis
(74) *Attorney, Agent, or Firm* — Christensen O'Connor Johnson Kindness PLLC

(57) ABSTRACT

A crystal of a compound represented by the general formula (I) or a pharmacologically acceptable salt thereof has an excellent LCAT-activating effect and is useful as an active ingredient in a therapeutic or prophylactic agent for arteriosclerosis, arteriosclerotic heart disease, coronary heart disease (including heart failure, myocardial infarction, angina pectoris, cardiac ischemia, cardiovascular disturbance, and restenosis caused by angiogenesis), cerebrovascular disease (including stroke and cerebral infarction), peripheral vascular disease (including diabetic vascular complications), dyslipidemia, hypo-HDL-cholesterolemia, or renal disease, particularly, an anti-arteriosclerotic agent, wherein $R^1$ is a hydrogen atom or a hydroxy group, and R is a 2-(trifluoromethyl)pyrimidin-5-yl group or a 5-(trifluoromethyl)pyrazin-2-yl group.

24 Claims, 7 Drawing Sheets

(56) References Cited

OTHER PUBLICATIONS

Official Letter dated Oct. 19, 2016, issued in corresponding Colombian Application No. 16-166.914, filed Dec. 12, 2016, 5 pages.
Ross, R., "Cell Biology of Atherosclerosis," Annual Reviews of Physiology 57:791-804, Mar. 1995.
Steinberg, D., "Low Density Lipoprotein Oxidation and Its Pathobiological Significance," Journal of Biological Chemistry 272(34):20963-20966, Aug. 1997.
Yvan-Charvet, L., et al., "Inhibition of Cholesteryl Ester Transfer Protein by Torcetrapib Modestly Increases Macrophage Cholesterol Efflux to HDL," Arteriosclerosis, Thrombosis, and Vascular Biology 27(5):1132-1138, May 2007.
International Search Report and Written Opinion dated Aug. 30, 2016, issued in corresponding International Application No. PCT/JP2016/067307, filed Jun. 10, 2016, 14 pages.
International Preliminary Report on Patentability dated Dec. 12, 2017, issued in corresponding International Application No. PCT/JP2016/067307, filed Jun. 10, 2016, 5 pages.

[Figure 1]
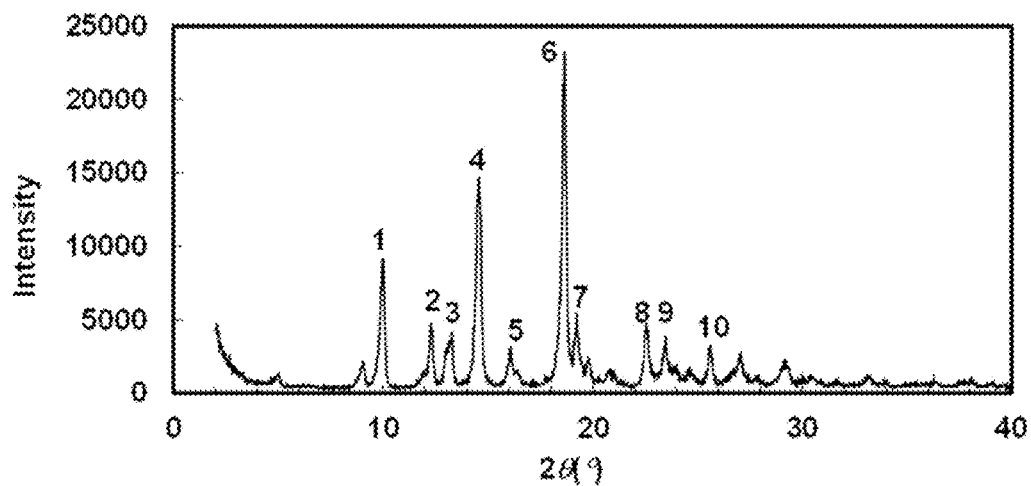
[Figure 2]
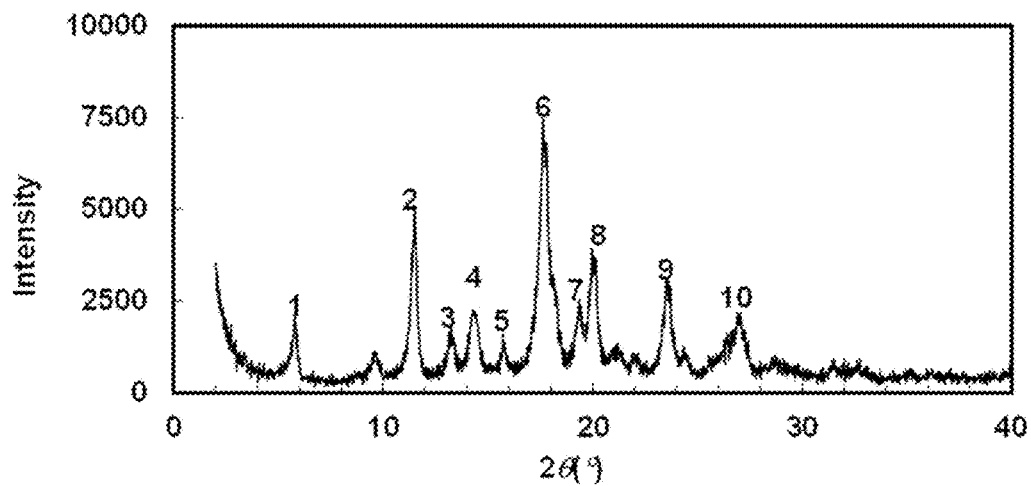

[Figure 3]
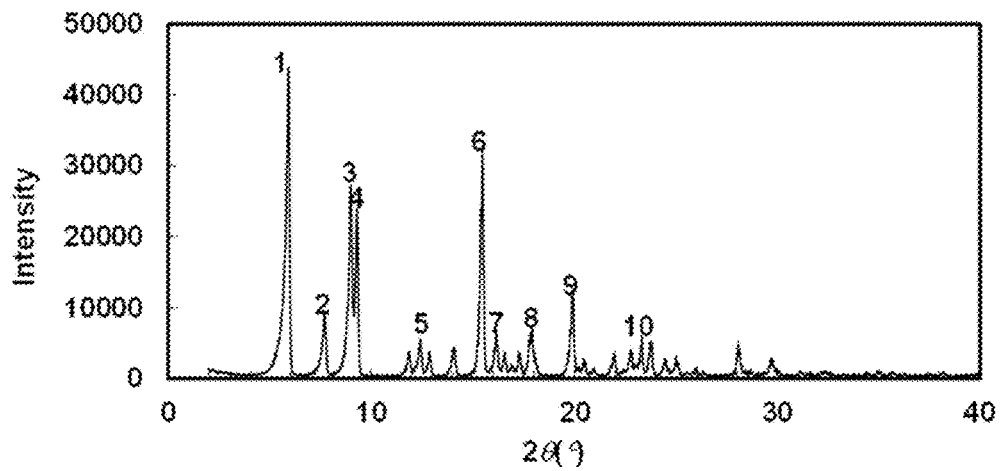
[Figure 4]
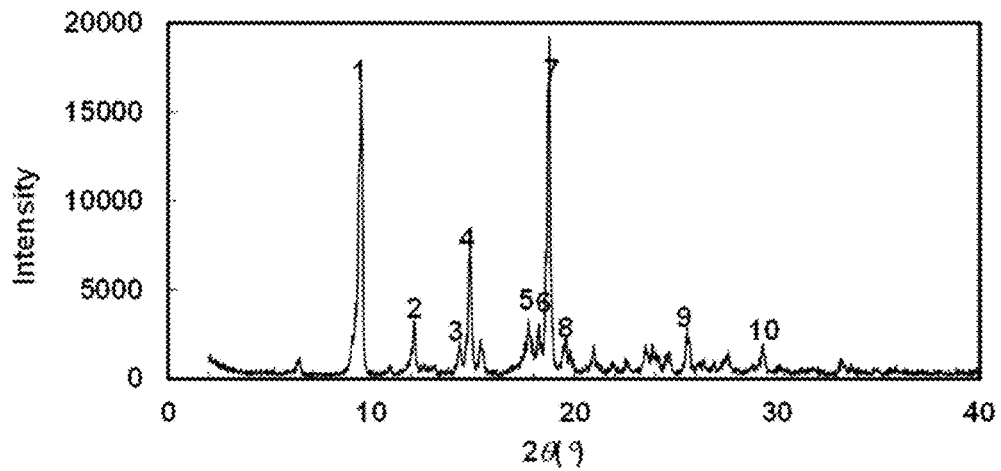

[Figure 5]
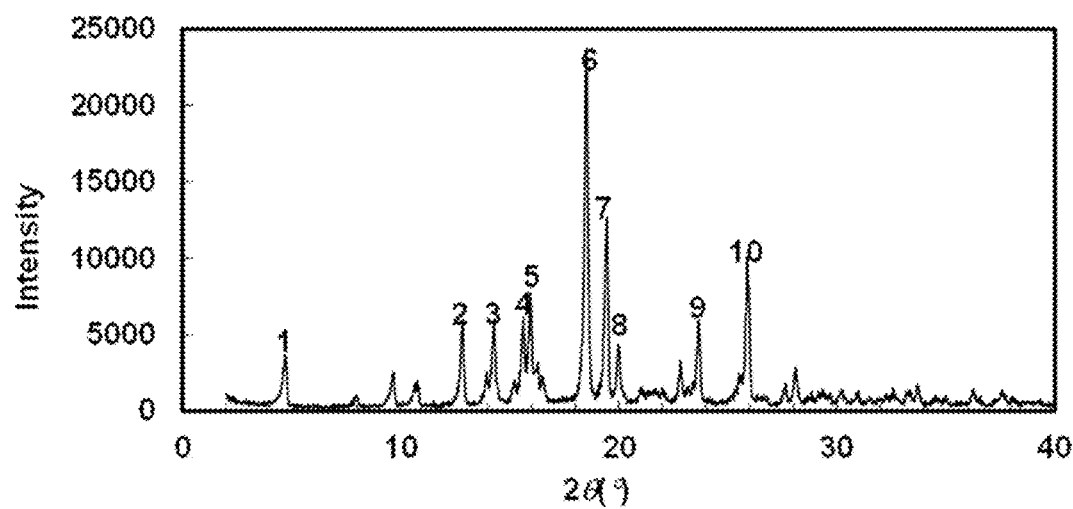
[Figure 6]
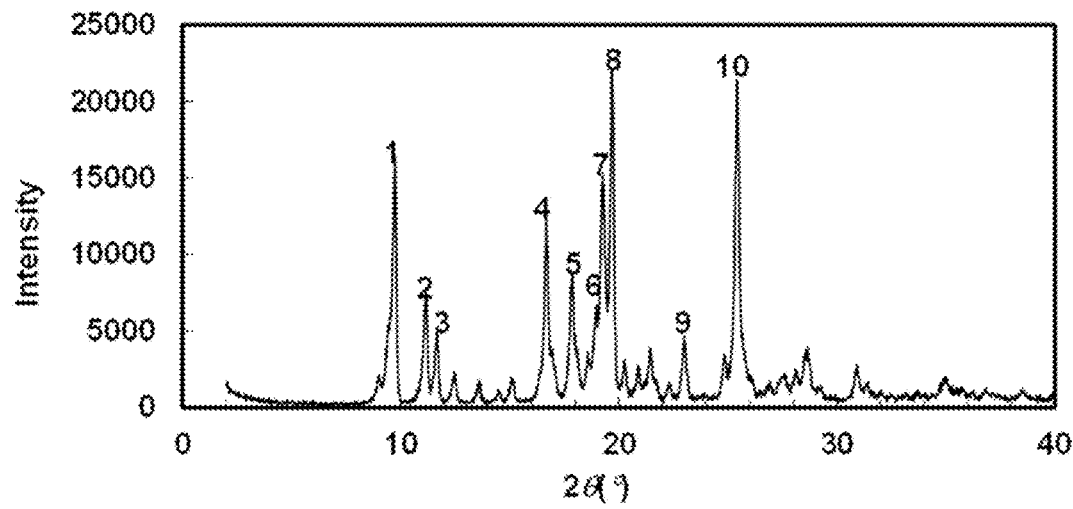

[Figure 7]
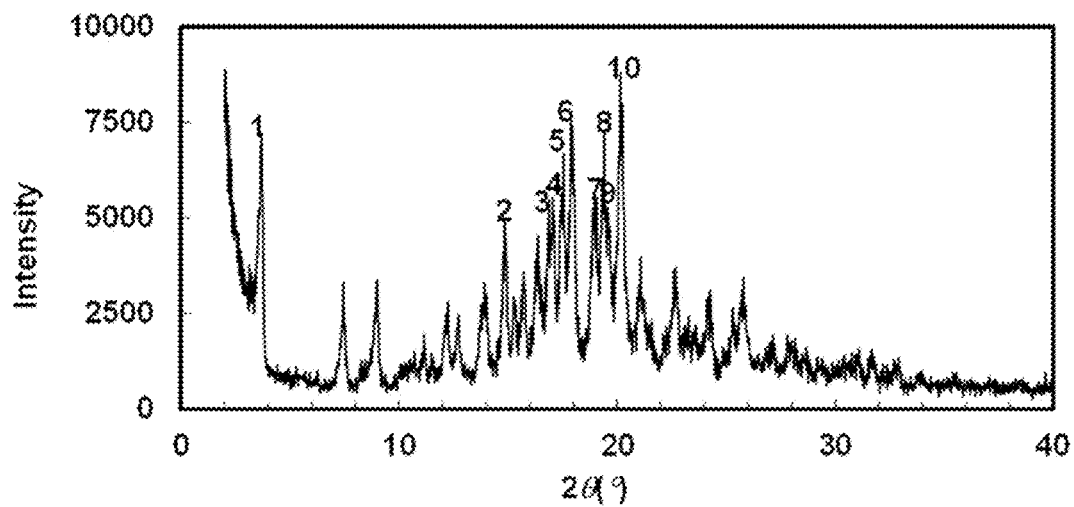
[Figure 8]
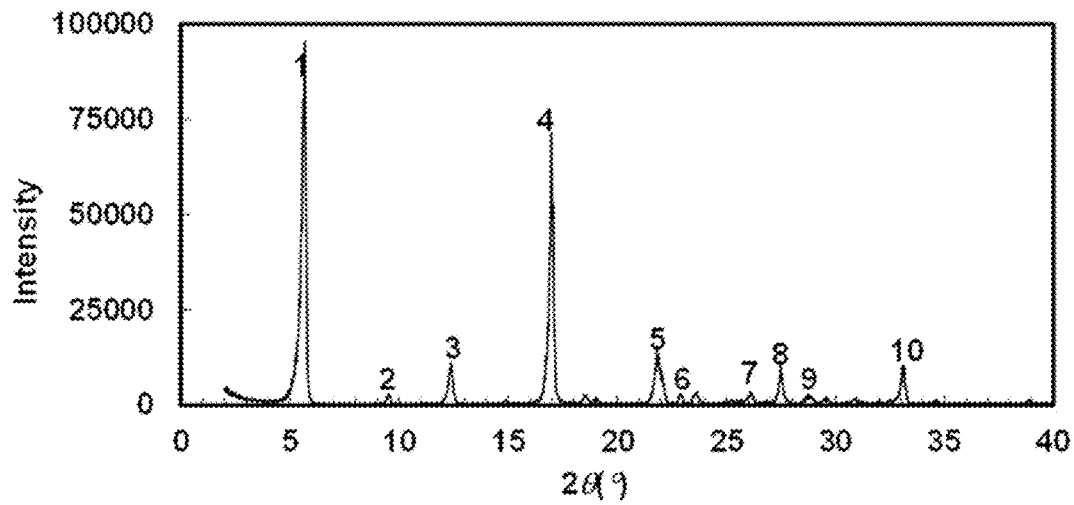

[Figure 9]
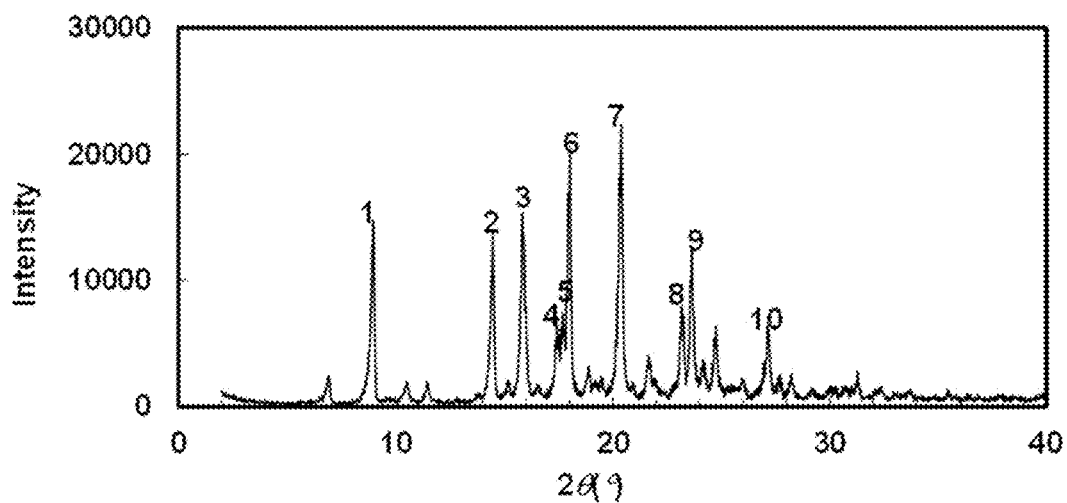
[Figure 10]
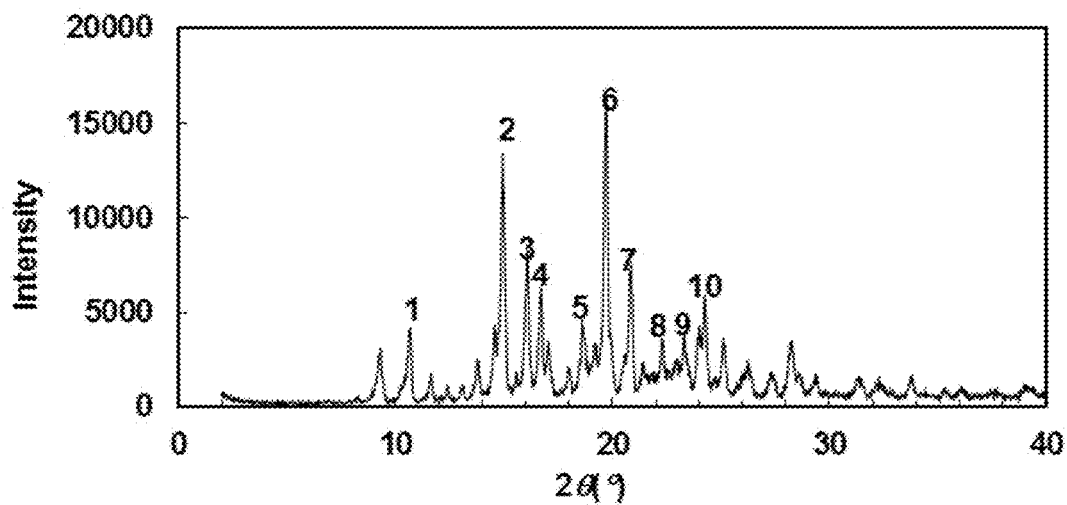

[Figure 11]
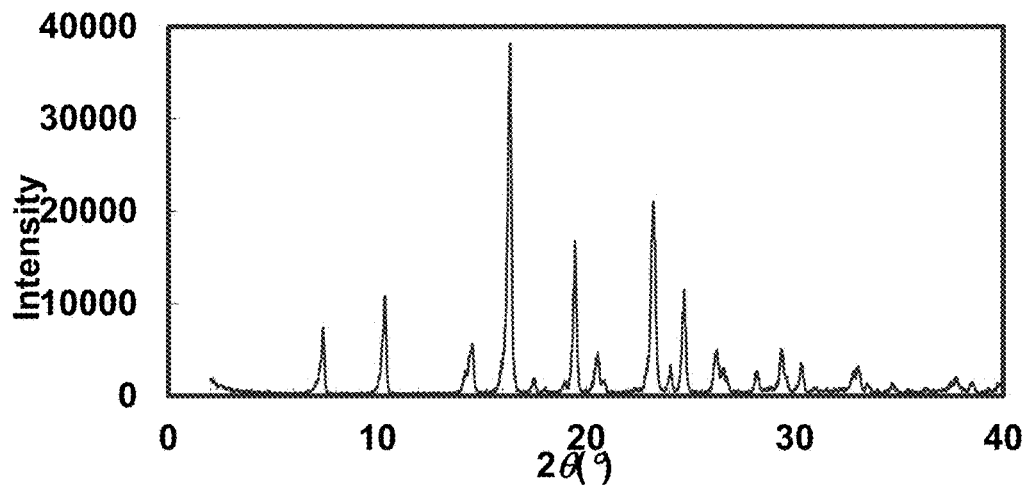
[Figure 12]
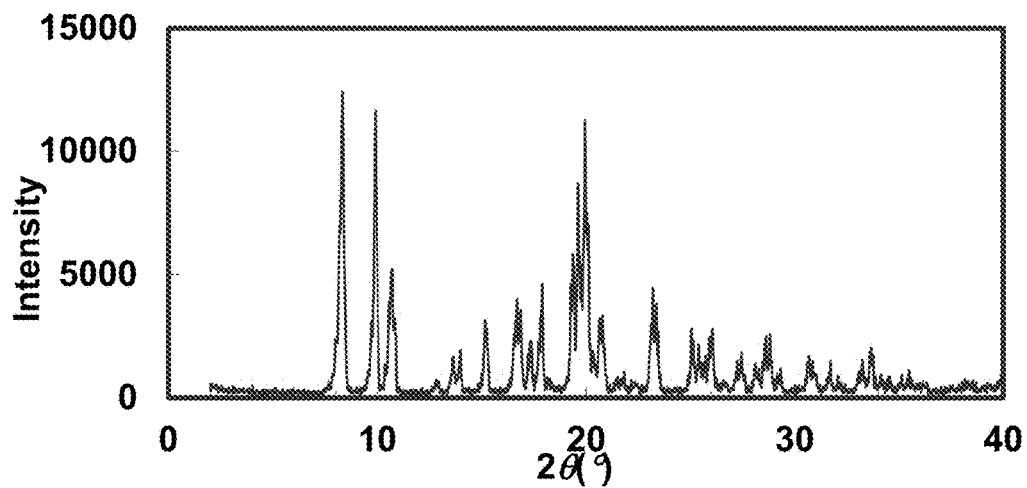

[Figure 13]
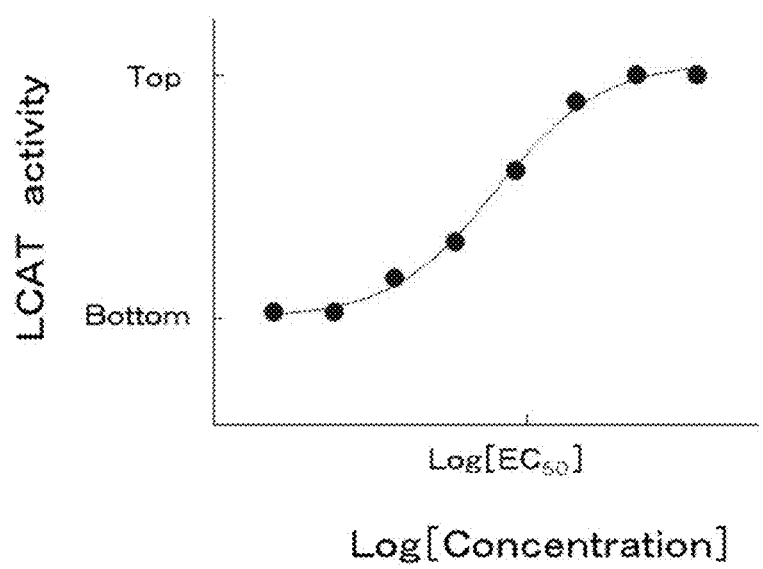

CRYSTAL OF 5-HYDROXY-4-(TRIFLUOROMETHYL) PYRAZOLOPYRIDINE DERIVATIVE

TECHNICAL FIELD

The present invention relates to a particular crystal of a pyrazolopyridine derivative or a pharmacologically acceptable salt thereof which has an excellent lecithin-cholesterol acetyltransferase (hereinafter, referred to as LCAT)-activating effect (preferably, reversible LCAT-activating effect).

BACKGROUND ART

Cardiovascular diseases (e.g., cardiac disease, cerebrovascular disease, and renal disease) caused by hypertension, dyslipidemia, diabetes mellitus, or the like are significant problems for developed countries. Antihypertensive, antidyslipidemic, and antidiabetic drugs are used in the treatment of the diseases hypertension, dyslipidemia, and hyperglycemia, respectively. In the clinical setting, α and β blockers, diuretics, calcium antagonists, ACE inhibitors, and A-II antagonists, etc. are used as antihypertensive drugs; HMG-CoA reductase inhibitors, anion exchange resins, nicotinic acid derivatives, probucol, and fibrates, etc. are used as antidyslipidemic drugs; and insulins, sulfonylureas, metformin, glitazones, and DPP4 inhibitors, etc. are used as antidiabetic drugs. These drugs contribute to the regulation of blood pressure and lipid or glucose levels in the blood. Nonetheless, even the use of these medicaments has not produced a great improvement in the death rates attributed to cardiac disease, cerebrovascular disease, and renal disease. Thus, there is a need for the development of better therapeutic drugs for these diseases.

A direct risk factor for cardiovascular diseases is atherosclerosis associated with thickening of the arterial wall. This thickening is caused by plaque formation resulting from the accumulation of oxidized low-density lipoprotein (hereinafter, referred to as LDL) cholesterol in macrophages and the like in the arterial wall (Non-patent Literatures 1 and 2). This plaque atherosclerosis inhibits blood flow and promotes the formation of blood clots.

The results of many epidemiologic studies indicate that serum concentrations of lipoproteins are associated with diseases such as dyslipidemia and arteriosclerosis (e.g., Non-patent Literature 3). Both an increased concentration of LDL cholesterol in the blood and a decreased concentration of high-density lipoprotein (hereinafter, referred to as HDL) cholesterol in the blood are risk factors for coronary diseases.

In peripheral tissues, HDL promotes efflux of cholesterol, which is in turn esterified by lecithin-cholesterol acetyltransferase (hereinafter, referred to as LCAT) on HDL to produce cholesteryl ester. Increased activity of LCAT promotes cholesterol efflux from macrophages (e.g., Non-patent Literatures 4 and 5). Accordingly, drugs that increase LCAT activity are considered to be useful as medicaments for the treatment or prophylaxis of diseases such as dyslipidemia and arteriosclerosis.

A peptide compound (e.g., Non-patent Literature 6) and, for example, the compound described in Patent Literature 1 as a small molecule, are known as such drugs that increase LCAT activity.

The compounds described in Patent Literatures 2 and 3 are known as compounds having a pyrazolopyridine skeleton.

CITATION LIST

Patent Literature

Patent Literature 1: WO2008/002591
Patent Literature 2: WO2012/028243
Patent Literature 3: WO2013/187462

Non-Patent Literature

Non-patent Literature 1: Ross, R., Annu. Rev. Physiol. 1995, Vol. 57, p. 791-804
Non-patent Literature 2: Steinberg, D., J. Biol. Chem. 1997, Vol. 272, p. 20963-20966
Non-patent Literature 3: Badimon, J. Clin. Invest., 1990, Vol. 85, p. 1234-1241
Non-patent Literature 4: Matsuura, F., J. Clin. Invest. 2006, Vol. 116, p. 1435-1442
Non-patent Literature 5: Yvan-Charvet, L., Arterioscler. Thromb. Vasc. Biol. 2007, Vol. 27, p. 1132-1138
Non-patent Literature 6: Iwata, A., Atherosclerosis. 2011, Vol. 218, p. 300-307

SUMMARY OF INVENTION

Technical Problem

Currently known compounds having an LCAT-activating effect are less than satisfactory in terms of safety and efficacy. Thus, there has been a strong demand for LCAT activators excellent in safety and efficacy.

Solution to Problem

The present inventors have conducted various syntheses and studies with the aim of obtaining a novel anti-arteriosclerotic drug that has an excellent LCAT-activating effect and directly promotes the efflux of cholesterol from macrophages. As a result, the present inventors have completed the present invention by finding that a pyrazolopyridine derivative having a particular structure or a pharmacologically acceptable salt thereof has an excellent LCAT-activating effect.

The present invention provides a particular crystal of a pyrazolopyridine derivative or a pharmacologically acceptable salt thereof which has an excellent LCAT-activating effect (preferably, reversible LCAT-activating effect), and a medicament comprising the same.

Specifically, the present invention relates to:
(1) a crystal of a compound represented by the general formula (I) or a pharmacologically acceptable salt thereof:

[Formula 1]

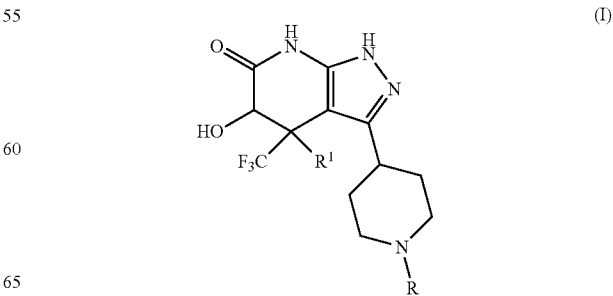

wherein R¹ represents a hydrogen atom or a hydroxy group, and R represents a 2-(trifluoromethyl)pyrimidin-5-yl group or a 5-(trifluoromethyl)pyrazin-2-yl group;

(2) the crystal according to (1), wherein R¹ is a hydrogen atom, and R is a 2-(trifluoromethyl)pyrimidin-5-yl group;

(3) the crystal according to (1), wherein R¹ is a hydroxy group, and R is a 5-(trifluoromethyl)pyrazin-2-yl group;

(4) a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one or (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one, or a hydrate thereof;

(5) a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate which exhibit main peaks at d-spacings of 8.86, 7.19, 6.67, 6.07, 5.51, 4.76, 4.61, 3.94, 3.79, and 3.47 angstroms in a powder X-ray diffraction pattern obtained by exposure to copper Kα radiation;

(6) a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate which exhibits main peaks at d-spacings of 15.28, 7.70, 6.67, 6.17, 5.62, 5.01, 4.58, 4.43, 3.77, and 3.30 angstroms in a powder X-ray diffraction pattern obtained by exposure to copper Kα radiation;

(7) a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate which exhibits main peaks at d-spacings of 14.97, 11.50, 9.84, 9.50, 7.12, 5.73, 5.48, 4.95, 4.46, and 3.81 angstroms in a powder X-ray diffraction pattern obtained by exposure to copper Kα radiation;

(8) a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate which exhibits main peaks at d-spacings of 9.28, 7.28, 6.16, 5.96, 4.99, 4.86, 4.73, 4.53, 3.48, and 3.04 angstroms in a powder X-ray diffraction pattern obtained by exposure to copper Kα radiation;

(9) a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one which exhibits main peaks at d-spacings of 18.79, 6.90, 6.21, 5.68, 5.56, 4.79, 4.56, 4.44, 3.76, and 3.44 angstroms in a powder X-ray diffraction pattern obtained by exposure to copper Kα radiation;

(10) a crystal of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate which exhibits main peaks at d-spacings of 9.09, 7.94, 7.58, 5.31, 4.97, 4.68, 4.60, 4.50, 3.86, and 3.50 angstroms in a powder X-ray diffraction pattern obtained by exposure to copper Kα radiation;

(11) a crystal of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate which exhibits main peaks at d-spacings of 23.99, 5.96, 5.25, 5.19, 5.07, 4.94, 4.68, 4.58, 4.52, and 4.40 angstroms in a powder X-ray diffraction pattern obtained by exposure to copper Kα radiation;

(12) a crystal of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one which exhibits main peaks at d-spacings of 15.60, 9.26, 7.14, 5.21, 4.07, 3.88, 3.41, 3.24, 3.11, and 2.70 angstroms in a powder X-ray diffraction pattern obtained by exposure to copper Kα radiation;

(13) a crystal of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one which exhibits main peaks at d-spacings of 9.88, 6.11, 5.58, 5.09, 5.01, 4.92, 4.35, 3.83, 3.76, and 3.28 angstroms in a powder X-ray diffraction pattern obtained by exposure to copper Kα radiation;

(14) a crystal of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one which exhibits main peaks at d-spacings of 8.29, 5.92, 5.51, 5.30, 4.76, 4.50, 4.26, 3.98, 3.81, and 3.66 angstroms in a powder X-ray diffraction pattern obtained by exposure to copper Kα radiation;

(15) a crystal of (+)-cis-5R-hydroxy-4R-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one which exhibits main peaks at d-spacings of 12.00, 8.53, 6.10, 5.42, 4.56, 4.32, 3.83, 3.60, 3.39, and 3.04 angstroms in a powder X-ray diffraction pattern obtained by exposure to copper Kα radiation;

(16) a crystal of (+)-cis-5R-hydroxy-4R-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate which exhibits main peaks at d-spacings of 10.62, 8.93, 8.26, 5.32, 5.25, 4.96, 4.58, 4.52, 4.44, and 3.84 angstroms in a powder X-ray diffraction pattern obtained by exposure to copper Kα radiation;

(17) a pharmaceutical composition comprising a crystal according to any one of (1) to (16) as an active ingredient;

(18) the pharmaceutical composition according to (17), wherein the pharmaceutical composition is for the treatment or prophylaxis of arteriosclerosis, arteriosclerotic heart disease, coronary heart disease, cerebrovascular disease, peripheral vascular disease, dyslipidemia, hypo-HDL-cholesterolemia, or renal disease;

(19) the pharmaceutical composition according to (17), wherein the pharmaceutical composition is for the treatment or prophylaxis of arteriosclerosis;

(20) the pharmaceutical composition according to (17), wherein the pharmaceutical composition is for the treatment or prophylaxis of dyslipidemia;

(21) the pharmaceutical composition according to (17), wherein the pharmaceutical composition is for the treatment or prophylaxis of a disease caused by an increased concentration of LDL cholesterol in the blood;

(22) the pharmaceutical composition according to (17), wherein the pharmaceutical composition is for the treatment or prophylaxis of a disease caused by a decreased concentration of HDL cholesterol in the blood;

(23) an LCAT activator comprising a crystal according to any one of (1) to (16) as an active ingredient;

(24) a reversible LCAT activator comprising a crystal according to any one of (1) to (16) as an active ingredient;

(25) an anti-arteriosclerotic agent comprising a crystal according to any one of (1) to (16) as an active ingredient;

(26) a prophylactic or therapeutic agent for arteriosclerosis, comprising a crystal according to any one of (1) to (16) as an active ingredient;

(27) an agent for lowering the concentration of LDL cholesterol in the blood, comprising a crystal according to any one of (1) to (16) as an active ingredient;

(28) an agent for elevating the concentration of HDL cholesterol in the blood, comprising a crystal according to any one of (1) to (16) as an active ingredient;
(29) a pharmaceutical composition comprising a crystal according to any one of (1) to (16) and a pharmacologically acceptable carrier;
(30) use of a crystal according to any one of (1) to (16) for the production of a pharmaceutical composition;
(31) the use according to (30), wherein the use is for the production of a pharmaceutical composition for the treatment or prophylaxis of arteriosclerosis, arteriosclerotic heart disease, coronary heart disease, cerebrovascular disease, peripheral vascular disease, dyslipidemia, hypo-HDL-cholesterolemia, or renal disease;
(32) the use according to (30), wherein the use is for the production of a pharmaceutical composition for the treatment or prophylaxis of arteriosclerosis;
(33) the use according to (30), wherein the use is for the production of a pharmaceutical composition for the treatment or prophylaxis of dyslipidemia;
(34) the use according to (30), wherein the use is for the production of a pharmaceutical composition for the treatment or prophylaxis of a disease caused by an increased concentration of LDL cholesterol in the blood;
(35) the use according to (30), wherein the use is for the production of a pharmaceutical composition for the treatment or prophylaxis of a disease caused by a decreased concentration of HDL cholesterol in the blood;
(36) a method for activating LCAT, comprising administering an effective amount of a crystal according to any one of (1) to (16) to a human;
(37) a method for treatment or prophylaxis of a disease, comprising administering an effective amount of a crystal according to any one of (1) to (16) to a human;
(38) the method according to (37), wherein the disease is arteriosclerosis, arteriosclerotic heart disease, coronary heart disease, cerebrovascular disease, peripheral vascular disease, dyslipidemia, hypo-HDL-cholesterolemia, or renal disease;
(39) the method according to (37), wherein the disease is arteriosclerosis;
(40) the method according to (37), wherein the disease is dyslipidemia;
(41) the method according to (37), wherein the disease is a disease caused by an increased concentration of LDL cholesterol in the blood;
(42) the method according to (37), wherein the disease is a disease caused by a decreased concentration of HDL cholesterol in the blood;
(43) the crystal according to any one of (1) to (16) for use in a method for treatment or prophylaxis of a disease;
(44) the crystal according to (43), wherein the disease is arteriosclerosis, arteriosclerotic heart disease, coronary heart disease, cerebrovascular disease, peripheral vascular disease, dyslipidemia, hypo-HDL-cholesterolemia, or renal disease;
(45) the crystal according to (43), wherein the disease is arteriosclerosis;
(46) the crystal according to (43), wherein the disease is dyslipidemia;
(47) the crystal according to (43), wherein the disease is a disease caused by an increased concentration of LDL cholesterol in the blood; and
(48) the crystal according to (43), wherein the disease is a disease caused by a decreased concentration of HDL cholesterol in the blood.

Hereinafter, compound (I) of the present invention will be described.

The compound (I) of the present invention encompasses both of a compound represented by the formula (I) and a compound represented by the formula (Ix), which is a tautomer thereof:

[Formula 2]

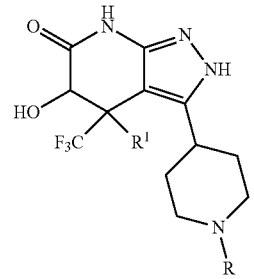

In the present application, a compound (I) including any such tautomer is also represented by the structural formula (I) and its corresponding chemical name for the sake of convenience, unless otherwise specified. The compound (I) of the present application also encompasses any isomer of an additional tautomer (amide-imide acid) of the compound (I) of the present invention. In the present application, a compound (I) including any such tautomer is also represented by the structural formula (I) and its corresponding chemical name for the sake of convenience.

The compound (I) of the present invention has a basic group and can therefore form an acid-addition salt with a pharmacologically acceptable acid. In the present invention, examples of the "pharmacologically acceptable salt thereof" can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornithine salt, glutamate, and aspartate.

The compound (I) of the present invention or the pharmacologically acceptable salt thereof, when left in the atmosphere, may form a hydrate by absorbing water. Such hydrates are also included in the scope of the present invention.

The compound (I) of the present invention or the pharmacologically acceptable salt thereof, when left in a solvent, may form a solvate. Such solvates are also included in the scope of the present invention.

The compound (I) of the present invention has optical isomers based on the asymmetric center in the molecule. These isomers of the compound of the present invention and mixtures of these isomers are all represented by a single formula, i.e., the general formula (I), unless otherwise specified. Thus, it should be understood that even these isomers and mixtures of these isomers are all included in the scope of the present invention.

The compound (I) of the present invention may contain isotope(s) of one or more atoms constituting such a compound at a non-natural ratio. Examples of the isotope include deuterium ($^2H$), tritium ($^3H$), iodine-125 ($^{125}I$), and carbon- 14 ($^{14}$C). Alternatively, the compound may be radiolabeled with a radioisotope, for example, tritium ($^3$H), iodine-125 ($^{125}$I), or carbon-14 ($^{14}$C). Such a radiolabeled compound is useful as a therapeutic or prophylactic agent, a research reagent, for example, an assay reagent, and a diagnostic agent, for example, an in vivo diagnostic imaging agent. It should be understood that all isotopic variants of the compound of the present invention are included in the scope of the present invention, regardless of being radioactive or not.

In the present invention, a salt of the compound (I) or a hydrate or a solvate thereof may form a plurality of crystals having different internal structures and physicochemical properties (crystal polymorphs) depending on reaction conditions and crystallization conditions. Each of these crystals or a mixture thereof at an arbitrary ratio is included in the scope of the present invention. A crystalline solid and an amorphous solid may coexist with each other. A mixture of these solids at an arbitrary ratio is included in the scope of the present invention. Specifically, the crystals of the present invention having a particular crystal form may contain crystals having another crystal form or an amorphous solid. The content of the particular crystal form is preferably 50% or more, more preferably 80% or more, even more preferably 90% or more, further preferably 93% or more, particularly preferably 95% or more, most preferably 97% or more.

In the present invention, the crystals refer to a solid whose internal structure is formed by a three-dimensionally regular repetition of constituent atoms (or groups thereof), and are distinguished from an amorphous solid not having such a regular internal structure. Whether a certain solid is crystalline can be examined by well-known crystallographic methods (e.g., powder X-ray crystallography and differential scanning calorimetry). For example, the certain solid is subjected to powder X-ray crystallography using X-ray obtained by exposure to copper Kα radiation. When a clear peak is observed in the X-ray diffraction pattern, the solid is determined to be crystalline. When no clear peak is observed, the solid is determined to be amorphous. When the peak can be read, but is not clear (e.g., the peak is broad), the solid is determined as crystals having a low degree of crystallinity. Such crystals having a low degree of crystallinity are included in the crystals of the present invention.

In the powder X-ray crystallography using copper Kα radiation, a sample is usually exposed to copper Kα radiation (wherein Kα1 radiation and Kα2 radiation are not separated). The X-ray diffraction pattern can be obtained by analyzing diffraction derived from the Kα radiation, and can also be obtained by analyzing only Kα1 radiation-derived diffraction isolated from the diffraction derived from the Kα radiation. In the present invention, the powder X-ray diffraction pattern obtained by exposure to Kα radiation includes an X-ray diffraction pattern obtained by analyzing diffraction derived from the Kα radiation, and an X-ray diffraction pattern obtained by analyzing Kα1 radiation-derived diffraction, and is preferably an X-ray diffraction pattern obtained by analyzing Kα1 radiation-derived diffraction.

The crystals of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate of the compound (I) of the present invention can be, for example, crystals that exhibit main peaks at d-spacings of 8.86, 7.19, 6.67, 6.07, 5.51, 4.76, 4.61, 3.94, 3.79, and 3.47 angstroms in a powder X-ray diffraction pattern obtained by exposure to copper Kα radiation, as shown in FIG. 1. In this context, the main peaks are peaks having a relative intensity of 13 or larger when the intensity of the peak at the d-spacing of 4.76 angstroms is defined as 100. In the X-ray diffraction patterns of FIGS. 1 to 12 given below, the ordinate shows the diffraction intensity [count/sec (cps)], and the abscissa shows the diffraction angle 2θ (degree). Also, the d-spacing (angstrom) can be calculated according to the expression $2d \sin \theta = n\lambda$ wherein $n=1$. In this expression, the wavelength λ of the Kα radiation is 1.54 angstroms, and the wavelength λ of the Kα1 radiation is 1.541 angstroms. The position and relative intensity of the d-spacing may vary somewhat depending on measurement conditions, etc. Therefore, even if a d-spacing is slightly different from one disclosed herein, the identity of a crystal form can be confirmed appropriately by reference to the whole pattern of the spectrum.

The crystals of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate of the compound (I) of the present invention can be, for example, crystals that exhibit main peaks at d-spacings of 15.28, 7.70, 6.67, 6.17, 5.62, 5.01, 4.58, 4.43, 3.77, and 3.30 angstroms in a powder X-ray diffraction pattern obtained by exposure to copper Kα radiation, as shown in FIG. 2. In this context, the main peaks are peaks having a relative intensity of 20 or larger when the intensity of the peak at the d-spacing of 5.01 angstroms is defined as 100.

The crystals of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate of the compound (I) of the present invention can be, for example, crystals that exhibit main peaks at d-spacings of 14.97, 11.50, 9.84, 9.50, 7.12, 5.73, 5.48, 4.95, 4.46, and 3.81 angstroms in a powder X-ray diffraction pattern obtained by exposure to copper Kα radiation, as shown in FIG. 3. In this context, the main peaks are peaks having a relative intensity of 12 or larger when the intensity of the peak at the d-spacing of 14.97 angstroms is defined as 100.

The crystals of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate of the compound (I) of the present invention can be, for example, crystals that exhibit main peaks at d-spacings of 9.28, 7.28, 6.16, 5.96, 4.99, 4.86, 4.73, 4.53, 3.48, and 3.04 angstroms in a powder X-ray diffraction pattern obtained by exposure to copper Kα radiation, as shown in FIG. 4. In this context, the main peaks are peaks having a relative intensity of 11 or larger when the intensity of the peak at the d-spacing of 4.73 angstroms is defined as 100.

The crystals of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one non-hydrate of the compound (I) of the present invention can be, for example, crystals that exhibit main peaks at d-spacings of 18.79, 6.90, 6.21, 5.68, 5.56, 4.79, 4.56, 4.44, 3.76, and 3.44 angstroms in a powder X-ray diffraction pattern obtained by exposure to copper Kα radiation, as shown in FIG. 5. In this context, the main peaks are peaks having a relative intensity of 17 or larger when the intensity of the peak at the d-spacing of 4.79 angstroms is defined as 100.

The crystals of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate of the compound (I) of the present invention can be, for example, crystals that exhibit main peaks at d-spacings of 9.09, 7.94, 7.58, 5.31, 4.97, 4.68, 4.60, 4.50, 3.86, and 3.50 angstroms in a powder X-ray diffraction pattern obtained by exposure to copper Kα radiation, as shown in FIG. 6. In this context, the main peaks are peaks having a relative intensity of 20 or larger when the intensity of the peak at the d-spacing of 4.50 angstroms is defined as 100.

The crystals of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate of the compound (I) of the present invention can be, for example, crystals that exhibit main peaks at d-spacings of 23.99, 5.96, 5.25, 5.19, 5.07, 4.94, 4.68, 4.58, 4.52, and 4.40 angstroms in a powder X-ray diffraction pattern obtained by exposure to copper Kα radiation, as shown in FIG. 7. In this context, the main peaks are peaks having a relative intensity of 58 or larger when the intensity of the peak at the d-spacing of 4.40 angstroms is defined as 100.

The crystals of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one non-hydrate of the compound (I) of the present invention can be, for example, crystals that exhibit main peaks at d-spacings of 15.60, 9.26, 7.14, 5.21, 4.07, 3.88, 3.41, 3.24, 3.11, and 2.70 angstroms in a powder X-ray diffraction pattern obtained by exposure to copper Kα radiation, as shown in FIG. 8. In this context, the main peaks are peaks having a relative intensity of 4 or larger when the intensity of the peak at the d-spacing of 15.60 angstroms is defined as 100.

The crystals of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one non-hydrate of the compound (I) of the present invention can be, for example, crystals that exhibit main peaks at d-spacings of 9.88, 6.11, 5.58, 5.09, 5.01, 4.92, 4.35, 3.83, 3.76, and 3.28 angstroms in a powder X-ray diffraction pattern obtained by exposure to copper Kα radiation, as shown in FIG. 9. In this context, the main peaks are peaks having a relative intensity of 30 or larger when the intensity of the peak at the d-spacing of 4.35 angstroms is defined as 100.

The crystals of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one non-hydrate of the compound (I) of the present invention can be, for example, crystals that exhibit main peaks at d-spacings of 8.29, 5.92, 5.51, 5.30, 4.76, 4.50, 4.26, 3.98, 3.81, and 3.66 angstroms in a powder X-ray diffraction pattern obtained by exposure to copper Kα radiation, as shown in FIG. 10. In this context, the main peaks are peaks having a relative intensity of 23 or larger when the intensity of the peak at the d-spacing of 4.50 angstroms is defined as 100.

The crystals of (+)-cis-5R-hydroxy-4R-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one non-hydrate of the compound (I) of the present invention can be, for example, crystals that exhibit main peaks at d-spacings of 12.00, 8.53, 6.10, 5.42, 4.56, 4.32, 3.83, 3.60, 3.39, and 3.04 angstroms in a powder X-ray diffraction pattern obtained by exposure to copper Kα radiation, as shown in FIG. 11. In this context, the main peaks are peaks having a relative intensity of 11 or larger when the intensity of the peak at the d-spacing of 5.42 angstroms is defined as 100.

The crystals of (+)-cis-5R-hydroxy-4R-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate of the compound (I) of the present invention can be, for example, crystals that exhibit main peaks at d-spacings of 10.62, 8.93, 8.26, 5.32, 5.25, 4.96, 4.58, 4.52, 4.44, and 3.84 angstroms in a powder X-ray diffraction pattern obtained by exposure to copper Kα radiation, as shown in FIG. 12. In this context, the main peaks are peaks having a relative intensity of 28 or larger when the intensity of the peak at the d-spacing of 10.62 angstroms is defined as 100.

Advantageous Effects of Invention

The crystal of the compound represented by the general formula (I) of the present invention or the pharmacologically acceptable salt thereof has an excellent LCAT-activating effect and is useful as an active ingredient in a therapeutic or prophylactic agent for arteriosclerosis, arteriosclerotic heart disease, coronary heart disease (including heart failure, myocardial infarction, angina pectoris, cardiac ischemia, cardiovascular disturbance, and restenosis caused by angiogenesis), cerebrovascular disease (including stroke and cerebral infarction), peripheral vascular disease (including diabetic vascular complications), dyslipidemia, hypo-HDL-cholesterolemia, or renal disease, particularly, an anti-arteriosclerotic agent.

BRIEF DESCRIPTION OF DRAWING

FIG. 1 is a powder X-ray diffraction pattern of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate obtained in Example 1.

FIG. 2 is a powder X-ray diffraction pattern of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate obtained in Example 2.

FIG. 3 is a powder X-ray diffraction pattern of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate obtained in Example 3.

FIG. 4 is a powder X-ray diffraction pattern of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate obtained in Example 4.

FIG. 5 is a powder X-ray diffraction pattern of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one obtained in Example 5.

FIG. 6 is a powder X-ray diffraction pattern of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate obtained in Example 6.

FIG. 7 is a powder X-ray diffraction pattern of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate obtained in Example 7.

FIG. 8 is a powder X-ray diffraction pattern of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one obtained in Example 8.

FIG. 9 is a powder X-ray diffraction pattern of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one obtained in Example 9.

FIG. 10 is a powder X-ray diffraction pattern of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one obtained in Example 10.

FIG. 11 is a powder X-ray diffraction pattern of (+)-cis-5R-hydroxy-4R-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one obtained in Example 11.

FIG. 12 is a powder X-ray diffraction pattern of (+)-cis-5R-hydroxy-4R-(trifluoromethyl)-3-{1-[2-(trifluoromethyl)

pyrimidin-5-yl]piperidin-4-yl}-1,4,5,7-tetrahydro-6H-pyrazolo[3,4-b]pyridin-6-one hydrate obtained in Example 12.

FIG. 13 shows a dose-response curve for determining the 50% effective concentration ($EC_{50}$) of LCAT activation in Test Examples 1 and 2 of the present invention.

DESCRIPTION OF EMBODIMENTS

The compound (I) of the present invention can be produced by the methods described in the Examples.

In the production process of the compound (I) of the present invention, if necessary, the product of each step can be isolated as the free compound or a salt thereof from the reaction mixture after the completion of the reaction by a routine method, for example, (1) a method of directly concentrating the reaction solution, (2) a method of filtering off insoluble matter such as a catalyst and concentrating the filtrate, (3) a method of adding water and a solvent immiscible with water (e.g., dichloroethane, diethyl ether, ethyl acetate, or toluene) to the reaction solution to extract a product, or (4) a method of collecting a crystallized or precipitated product by filtration. The isolated product can be purified, if necessary, by a routine method, for example, recrystallization, reprecipitation, or various chromatography techniques. Alternatively, the product of each step may be used in the subsequent step without being isolated or purified.

The compound (I) of the present invention is isolated and purified as the free compound or a pharmacologically acceptable salt, a hydrate, or a solvate thereof. The pharmacologically acceptable salt of the compound (I) of the present invention can be produced through a salt-forming reaction of the compound (I) by a routine method. The isolation and purification are carried out by application of usual chemical operations such as extraction, concentration, distillation, crystallization, filtration, recrystallization, or various chromatography techniques.

Various isomers can be separated by exploiting differences in physicochemical properties between the isomers. For example, a racemic mixture can be converted to an optically pure isomer by, for example, fractionated crystallization for producing a diastereomer salt with an optically active base or acid or chromatography using a chiral column. Also, a diastereomeric mixture can be separated by, for example, fractionated crystallization or various chromatography techniques. Alternatively, an optically active compound can also be produced using an appropriate optically active starting material.

Examples of dosage forms of the compound represented by the general formula (I) of the present invention or the pharmacologically acceptable salt thereof can include: oral administration forms such as tablets, granules, powders, capsules, and syrups; and parenteral administration forms such as injections and suppositories. These formulations can be administered systemically or locally.

Examples of forms of oral medicaments comprising the compound represented by the general formula (I) of the present invention or the pharmacologically acceptable salt thereof include tablets, pills, granules, powders, capsules, solutions, suspension, emulsions, syrups, and elixirs. Examples of forms of parenteral medicaments comprising the compound represented by the general formula (I) of the present invention or the pharmacologically acceptable salt thereof include injections, ointments, gels, creams, patches, aerosols, inhalants, sprays, eye drops, and suppositories. The medicaments in these forms can be prepared according to a routine method using additives appropriately selected according to need from pharmaceutically acceptable additives such as excipients, binders, diluents, stabilizers, antiseptics, colorants, solubilizers, suspending agents, buffers, and wetting agents.

The dose at which the compound represented by the general formula (I) of the present invention or the pharmacologically acceptable salt thereof is administered differs depending on the symptoms, body weight, and age of the recipient (a warm-blooded animal, for example, a human), the administration method, etc. For example, in the case of oral administration, a single dose is 0.01 mg/kg body weight (preferably 0.03 mg/kg body weight) as the lower limit and 300 mg/kg body weight (preferably 100 mg/kg body weight) as the upper limit and is desirably administered one to several times a day according to the symptoms. In the case of intravenous administration, a single dose is 0.01 mg/kg body weight (preferably 0.03 mg/kg body weight) as the lower limit and 300 mg/kg body weight (preferably 100 mg/kg body weight) as the upper limit and is desirably administered one to several times a day according to the symptoms.

Hereinafter, the present invention will be described in more detail with reference to Examples, Test Examples, and Formulation Examples. However, the scope of the present invention is not intended to be limited by these. In the Examples given below, hexane represents n-hexane; THF represents tetrahydrofuran; IPA represents 2-propanol; DMF represents N,N'-dimethylformamide; and DMSO represents dimethyl sulfoxide.

EXAMPLES (Example 1) (+)-4,5-Dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate (1) tert-Butyl 4-[5-amino-1-(diphenylmethyl)-1H-pyrazol-3-yl]piperidine-1-carboxylate

[Formula 3]

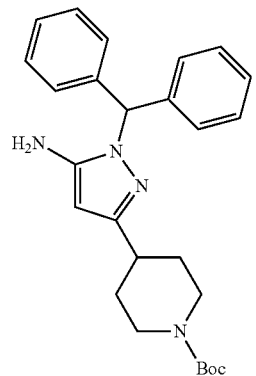

Diphenylmethyl hydrazine hydrochloride (8.57 g, 36.5 mmol) was added to a solution of tert-butyl 4-(cyanoacetyl)piperidine-1-carboxylate (compound described in the pamphlet of WO2004/14910, 7.1 g, 28 mmol) in ethanol (71 mL), and the mixture was stirred at 50° C. for 1 hour. The reaction solution was concentrated under reduced pressure, and the obtained residue was separated into organic and aqueous layers by the addition of a saturated sodium bicarbonate aqueous solution and ethyl acetate. The organic layer was dried over anhydrous magnesium sulfate, and the solvent was distilled off under reduced pressure. The obtained residue was purified by silica gel column chromatography [elute: hexane/ethyl acetate=95/5-40/60 (gradient)] to obtain the title compound (7.43 g, yield: 59%).

$^1$H-NMR (400 Hz, CDCl$_3$) δ: 7.37-7.19 (10H, m), 6.66 (1H, s), 5.40 (1H, s), 4.11 (1H, brs), 3.23-3.20 (1H, m), 2.82-2.65 (3H, m), 1.89-1.86 (2H, m), 1.61-1.52 (4H, m), 1.46 (9H, s).

(2) tert-Butyl 4-[4,5-dihydroxy-6-oxo-4-(trifluoromethyl)-4,5,6,7-tetrahydro-1H-pyrazolo[3,4-b]pyridin-3-yl]piperidine-1-carboxylate

[Formula 4]

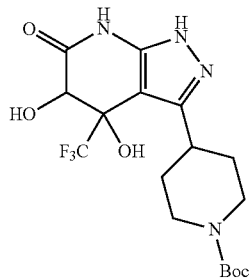

A solution of ethyl 2-triethylsilyloxyacetate (compound described in the literature J. Org. Chem., 2008, Vol. 73, p. 6268-6278, 18.37 g, 84.13 mmol) and ethanol (0.1474 mL, 2.524 mmol) in toluene (40 mL) was added at room temperature to a suspension of sodium hydride (63% dispersion in oil, 5.127 g, 134.6 mmol) in toluene (80 mL), subsequently a solution of ethyl trifluoroacetate (15.07 mL, 126.2 mmol) in toluene (20 mL) was added thereto, and the mixture was stirred for 5 minutes and then stirred at 80° C. for 30 minutes. To the reaction solution, a saturated ammonium chloride aqueous solution was added under ice cooling, followed by extraction with ethyl acetate. The obtained organic layer was washed with brine and dried over anhydrous sodium sulfate, and the solvent was distilled off under reduced pressure to obtain a crude oil product (23.6 g).

A mixed solution of the crude oil product (23.6 g) obtained by the procedures described above and tert-butyl 4-[5-amino-1-(diphenylmethyl)-1H-pyrazol-3-yl]piperidine-1-carboxylate (10.83 g, 25.04 mmol) produced in (1) in ethanol (150 mL) and acetic acid (50 mL) was stirred for 4 hours under heating to reflux. The solvent in the reaction solution was distilled off under reduced pressure, and ethyl acetate was added to the obtained residue. The organic layer was washed with a saturated sodium bicarbonate aqueous solution and brine in this order and dried over anhydrous sodium sulfate, and the solvent was distilled off under reduced pressure. Ethyl acetate and hexane were added to the obtained residue, and the resulting precipitate was collected by filtration to obtain a solid. The solvent in the filtrate was further distilled off under reduced pressure. The obtained residue was purified by silica gel column chromatography [elute: hexane/ethyl acetate=90/10-50/50 (gradient)] and combined with the preliminarily obtained solid to obtain a synthesis intermediate.

Triethylsilane (10.7 mL, 67.4 mmol) and trifluoroacetic acid (90 mL, 1176 mmol) were added to a suspension of the synthesis intermediate obtained by the procedures described above in dichloromethane (300 mL), and the mixture was stirred at room temperature for 2 hours. The solvent in the reaction solution was distilled off under reduced pressure. To the obtained residue, diethyl ether and hexane were added, and the mixture was stirred for 30 minutes. The resulting precipitate was collected by filtration to obtain a colorless solid.

A solution of di-t-butyl dicarbonate (5.53 g, 25.4 mmol) and triethylamine (4.69 mL, 33.8 mmol) in ethyl acetate (30 mL) was added at room temperature to a mixed suspension of the colorless solid obtained by the procedures described above in ethyl acetate (120 mL) and THF (40 mL), and the mixture was stirred at room temperature for 3 hours and left overnight at room temperature as it was. The reaction solution was washed with a saturated sodium bicarbonate aqueous solution and brine in this order and dried over anhydrous sodium sulfate, and the solvent was distilled off under reduced pressure. The obtained residue was purified by silica gel column chromatography [elute: hexane/ethyl acetate=50:50-0:100 (gradient)] to obtain the title compound (3.09 g, yield: 44%).

$^1$H-NMR (400 MHz, DMSO-d$_6$) δ: 12.24 (1H, s), 10.55 (1H, s), 6.76 (1H, s), 5.65 (1H, d, J=4 Hz), 4.33 (1H, brs), 4.13-3.99 (2H, m), 3.20-3.09 (1H, m), 2.84-2.59 (2H, m), 1.84-1.76 (1H, m), 1.66-1.46 (3H, m), 1.42 (9H, s).

(3) Optically active form of tert-butyl 4-[4,5-dihydroxy-6-oxo-4-(trifluoromethyl)-4,5,6,7-tetrahydro-1H-pyrazolo[3,4-b]pyridin-3-yl]piperidine-1-carboxylate

[Formula 5]

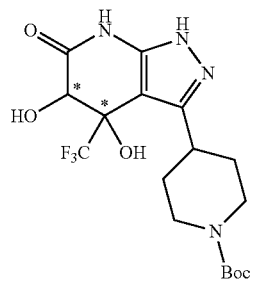

A mixed solution of tert-butyl 4-[4,5-dihydroxy-6-oxo-4-(trifluoromethyl)-4,5,6,7-tetrahydro-1H-pyrazolo[3,4-b]pyridin-3-yl]piperidine-1-carboxylate (0.79 g, 1.9 mmol) produced in (2) in ethyl acetate and methanol was adsorbed onto a silica gel, and the solvent was distilled off under reduced pressure. The obtained powder was purified by flash LC [column: Chiralflash IA (30 mm i.d.×100 mm); manufactured by Daicel Corporation, elute: hexane/IPA=90/10, flow rate: 12 mL/min] to obtain the title compound (0.34 g, yield: 43%, optically active form).

The optical purity was measured using HPLC [column: Chiralpak IA (4.6 mm i.d.×250 mm); manufactured by Daicel Corporation, elute: hexane/IPA=80/20, flow rate: 1.0 mL/min].

Optical purity: 99% or higher (retention time: 7.7 min).

(4) (+)-4,5-Dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one

[Formula 6]

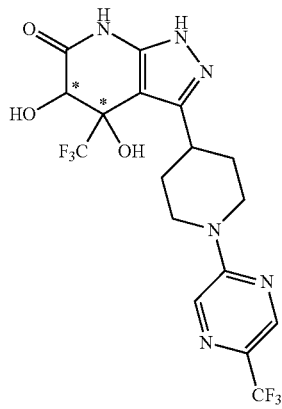

Trifluoroacetic acid (2 mL) was added at room temperature to a suspension of the optically active form of tert-butyl 4-[4,5-dihydroxy-6-oxo-4-(trifluoromethyl)-4,5,6,7-tetrahydro-1H-pyrazolo[3,4-b]pyridin-3-yl]piperidine-1-carboxylate (0.34 g, 0.81 mmol) produced in (3) in dichloromethane (6 mL), and the mixture was stirred for 2 hours. The solvent in the reaction solution was distilled off under reduced pressure, and the obtained residue was solidified by the addition of diethyl ether and hexane. The solvent was removed by decantation, and the obtained solid was dried under reduced pressure to obtain a synthesis intermediate.

2-Chloro-5-(trifluoromethyl)pyrazine (0.15 mL, 1.2 mmol) and N,N-diisopropylethylamine (0.41 mL, 2.4 mmol) were added at room temperature to a solution of the synthesis intermediate obtained by the procedures described above in DMSO (5 mL), and the mixture was stirred for 1 hour and then left overnight as it was. To the reaction solution, ethyl acetate was added. The organic layer was washed with water and brine in this order and dried over anhydrous sodium sulfate, and the solvent was distilled off under reduced pressure. The obtained residue was purified by silica gel column chromatography [elute: hexane/ethyl acetate=50/50-0/1000 (gradient)] to obtain the title compound (0.31 g, yield: 82%, optically active form).

The optical purity was measured using HPLC [column: Chiralpak IA (4.6 mm i.d.×250 mm); manufactured by Daicel Corporation, elute: hexane/IPA=60/40, flow rate: 1.0 mL/min].

Optical purity: 99% or higher (retention time: 6.7 min);
$^1$H-NMR (400 MHz, DMSO-$d_6$) δ: 12.21 (1H, s), 10.57 (1H, s), 8.51 (1H, s), 8.50 (1H, s), 6.81 (1H, s), 5.68 (1H, d, J=4 Hz), 4.69-4.56 (2H, m), 4.37-4.31 (1H, m), 3.46-3.34 (1H, m), 3.11-2.97 (2H, m), 1.98-1.88 (1H, m), 1.83-1.58 (3H, m);
MS (ESI) m/z: 467 (M+H)$^+$;
$[\alpha]_D^{25}$=+3.9° (DMF, c=0.924).

(5) (+)-4,5-Dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate Toluene (395 μl) was added to (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one (19.73 mg) produced in (4) at room temperature. Then, the mixture was stirred at 40° C. for approximately 20 hours and subsequently stirred at room temperature for approximately 0.5 hours. The solid was collected by filtration and dried overnight at room temperature to obtain the title compound (15.71 mg). Rate of recovery: 78%.

Elemental analysis value in terms of $C_{17}H_{16}F_6N_6O_3 \cdot 0.5H_2O$
Calcd: C, 42.95; H, 3.60; F, 23.98; N, 17.68.
Found: C, 42.97; H, 3.58; F, 23.79; N, 17.21.

Table 1 shows peaks having a relative intensity of 13 or larger when the largest peak intensity in the diffraction pattern of powder X-ray diffraction (CuKα, λ=1.54 angstroms, scanning rate=20°/min) in FIG. 1 is defined as 100.

TABLE 1

| Peak No. | 2θ | d value | Relative intensity |
|---|---|---|---|
| 1 | 9.98 | 8.86 | 40 |
| 2 | 12.30 | 7.19 | 21 |
| 3 | 13.26 | 6.67 | 17 |
| 4 | 14.58 | 6.07 | 64 |
| 5 | 16.08 | 5.51 | 13 |
| 6 | 18.64 | 4.76 | 100 |
| 7 | 19.24 | 4.61 | 22 |
| 8 | 22.56 | 3.94 | 21 |
| 9 | 23.48 | 3.79 | 14 |
| 10 | 25.62 | 3.47 | 15. |

(Example 2) (+)-4,5-Dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate (+)-4,5-Dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one (21.21 mg) produced in Example 1(4) was completely dissolved by the addition of 1,4-dioxane (2 ml) at room temperature. Then, the mixture was frozen in a freezer of –80° C., and then, the solvent was removed in a freeze dryer while the temperature was changed from –45° C. to 25° C. Subsequently, the glass vial containing the freeze-dried product was placed with the vial opened in a screw tube containing water, and the screw tube was hermetically sealed and then stored in a thermostat bath of 25° C. for 3 days. Then, the glass vial was taken out thereof and dried in air overnight to obtain the title compound.

Elemental analysis value in terms of $C_{17}H_{16}F_6N_6O_3 \cdot 1.8H_2O$
Calcd: C, 40.94; H, 3.96; F, 22.85; N, 16.85.
Found: C, 40.63; H, 3.83; F, 23.11; N, 16.57.

Table 2 shows peaks having a relative intensity of 20 or larger when the largest peak intensity in the diffraction pattern of powder X-ray diffraction (CuKα, λ=1.54 angstroms, scanning rate=20°/min) in FIG. 2 is defined as 100.

TABLE 2

| Peak No. | 2θ | d value | Relative intensity |
|---|---|---|---|
| 1 | 5.78 | 15.28 | 28 |
| 2 | 11.48 | 7.70 | 66 |
| 3 | 13.26 | 6.67 | 24 |
| 4 | 14.34 | 6.17 | 32 |
| 5 | 15.76 | 5.62 | 20 |
| 6 | 17.68 | 5.01 | 100 |

TABLE 2-continued

| Peak No. | 2θ | d value | Relative intensity |
|---|---|---|---|
| 7 | 19.36 | 4.58 | 34 |
| 8 | 20.04 | 4.43 | 52 |
| 9 | 23.58 | 3.77 | 43 |
| 10 | 26.98 | 3.30 | 30. |

(Example 3) (+)-4,5-Dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate Nitromethane (200 μl) was added to (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one (19.97 mg) produced in Example 1(4) at room temperature. Then, the mixture was stirred at 10° C. for approximately 20 hours and subsequently stirred at room temperature for approximately 0.5 hours. The solid was collected by filtration and dried overnight at room temperature to obtain the title compound (12.78 mg). Rate of recovery: 62%.

Elemental analysis value in terms of $C_{17}H_{16}F_6N_6O_3 \cdot 1.0H_2O$

Calcd: C, 42.16; H, 3.75; F, 23.53; N, 17.35.

Found: C, 42.47; H, 3.46; F, 23.65; N, 17.39.

Table 3 shows peaks having a relative intensity of 12 or larger when the largest peak intensity in the diffraction pattern of powder X-ray diffraction (CuKα, λ=1.54 angstroms, scanning rate=20°/min) in FIG. 3 is defined as 100.

TABLE 3

| Peak No. | 2θ | d value | Relative intensity |
|---|---|---|---|
| 1 | 5.90 | 14.97 | 100 |
| 2 | 7.68 | 11.50 | 22 |
| 3 | 8.98 | 9.84 | 63 |
| 4 | 9.30 | 9.50 | 57 |
| 5 | 12.42 | 7.12 | 14 |
| 6 | 15.46 | 5.73 | 72 |
| 7 | 16.16 | 5.48 | 15 |
| 8 | 17.90 | 4.95 | 14 |
| 9 | 19.90 | 4.46 | 25 |
| 10 | 23.30 | 3.81 | 12. |

(Example 4) (+)-4,5-Dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate Water (393 μl) was added to (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one (19.64 mg) produced in Example 1(4) at room temperature. Then, the mixture was stirred at 40° C. for approximately 20 hours and subsequently stirred at room temperature for approximately 0.5 hours. The solid was collected by filtration and then dried overnight at room temperature to obtain the title compound (14.93 mg). Rate of recovery: 71%.

Elemental analysis value in terms of $C_{17}H_{16}F_6N_6O_3 \cdot 1.75H_2O$

Calcd: C, 41.01; H, 3.95; F, 22.90; N, 16.88.

Found: C, 40.95; H, 3.81; F, 23.24; N, 16.66.

Table 4 shows peaks having a relative intensity of 11 or larger when the largest peak intensity in the diffraction pattern of powder X-ray diffraction (CuKα, λ=1.54 angstroms, scanning rate=20°/min) in FIG. 4 is defined as 100.

TABLE 4

| Peak No. | 2θ | d value | Relative intensity |
|---|---|---|---|
| 1 | 9.52 | 9.28 | 94 |
| 2 | 12.14 | 7.28 | 20 |
| 3 | 14.36 | 6.16 | 11 |
| 4 | 14.86 | 5.96 | 42 |
| 5 | 17.76 | 4.99 | 18 |
| 6 | 18.24 | 4.86 | 17 |
| 7 | 18.74 | 4.73 | 100 |
| 8 | 19.56 | 4.53 | 14 |
| 9 | 25.60 | 3.48 | 14 |
| 10 | 29.32 | 3.04 | 11. |

(Example 5) (+)-4,5-Dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one (+)-4,5-Dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one (20.40 mg) produced in Example 1(4) was treated by heating to 250° C. in a thermal analysis apparatus, and then, toluene (408 μl) was added thereto at room temperature. Then, the mixture was stirred at 10° C. for approximately 20 hours and subsequently stirred at room temperature for approximately 0.5 hours. The solid was collected by filtration and then dried overnight at room temperature to obtain the title compound (13.53 mg). Rate of recovery: 66%.

Elemental analysis value in terms of $C_{17}H_{16}F_6N_6O_3$

Calcd: C, 43.78; H, 3.46; F, 24.44; N, 18.02.

Found: C, 43.58; H, 3.41; F, 24.17; N, 17.78.

Table 5 shows peaks having a relative intensity of 17 or larger when the largest peak intensity in the diffraction pattern of powder X-ray diffraction (CuKα, λ=1.54 angstroms, scanning rate=20°/min) in FIG. 5 is defined as 100.

TABLE 5

| Peak No. | 2θ | d value | Relative intensity |
|---|---|---|---|
| 1 | 4.70 | 18.79 | 17 |
| 2 | 12.82 | 6.90 | 25 |
| 3 | 14.26 | 6.21 | 26 |
| 4 | 15.60 | 5.68 | 26 |
| 5 | 15.94 | 5.56 | 34 |
| 6 | 18.50 | 4.79 | 100 |
| 7 | 19.44 | 4.56 | 55 |
| 8 | 19.98 | 4.44 | 20 |
| 9 | 23.66 | 3.76 | 26 |
| 10 | 25.90 | 3.44 | 44. |

(Example 6) (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate (1) tert-Butyl 4-[1-(diphenylmethyl)-6-oxo-4-(trifluoromethyl)-4,5,6,7-tetrahydro-1H-pyrazolo[3,4-b]pyridin-3-yl]piperidine-1-carboxylate

[Formula 7]

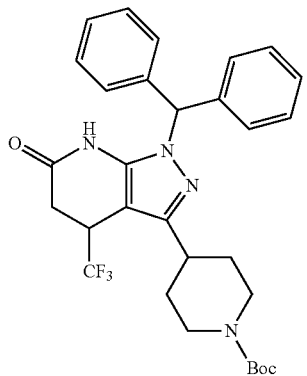

Trifluoroacetaldehyde ethyl hemiacetal (2.78 g, 17.3 mmol) was added to a solution of tert-butyl 4-[5-amino-1-(diphenylmethyl)-1H-pyrazol-3-yl]piperidine-1-carboxylate (2.50 g, 5.78 mmol) produced in Example 1(1) and Meldrum's acid (2.50 g, 17.3 mmol) in ethanol (50 mL), and the mixture was stirred for 3 hours under heating to reflux. The solvent in the reaction solution was distilled off under reduced pressure. The obtained residue was purified by silica gel column chromatography [NH-silica gel, elute: hexane/ethyl acetate=95/5-50/50 (gradient)], and a fraction containing the compound of interest was collected and powdered with ethyl acetate and hexane to obtain the title compound (1.48 g, yield: 46%).
$^1$H-NMR (400 Hz, CDCl$_3$) δ: 7.44-7.12 (10H, m), 6.69 (1H, s), 4.13 (1H, brs), 3.65-3.55 (1H, m), 2.95-2.69 (7H, m), 1.87-1.55 (4H, m), 1.45 (9H, s).

(2) Methyl 3-[1-(tert-butoxycarbonyl)piperidin-4-yl]-1-(diphenylmethyl)-5-hydroxy-6-oxo-4-(trifluoromethyl)-4,5,6,7-tetrahydro-1H-pyrazolo[3,4-b]pyridine-5-carboxylate

[Formula 8]

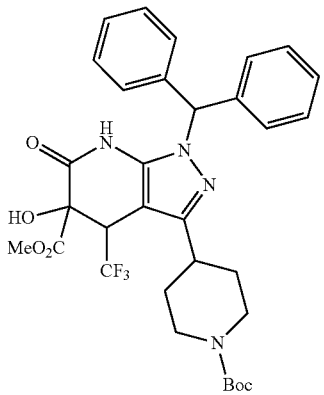

Lithium diisopropylamide (solution in hexane and THF, 14.5 mL, 15.8 mmol) was added dropwise at −78° C. to a solution of tert-butyl 4-[1-(diphenylmethyl)-6-oxo-4-(trifluoromethyl)-4,5,6,7-tetrahydro-1H-pyrazolo[3,4-b]pyridin-3-yl]piperidine-1-carboxylate (2.92 g, 5.27 mmol) produced in (1) and dimethyl carbonate (0.665 mL, 7.90 mmol) in THF (50 mL). After removal of the cooling bath, the mixture was stirred for 30 minutes while its temperature was spontaneously raised. To the reaction solution, a saturated ammonium chloride aqueous solution was added, followed by extraction with ethyl acetate three times. The obtained organic layer was dried over magnesium sulfate, and the solvent was distilled off under reduced pressure. The obtained residue was purified by silica gel chromatography [NH-silica gel, elute: dichloromethane/methanol=100/0-90/10 (gradient)] to obtain a synthesis intermediate.

1,8-Diazabicyclo[5.4.0]-7-undecene (hereinafter, referred to as DBU; 1.57 mL, 10.5 mmol), (1S)-(+)-(10-camphorsulfonyl)oxaziridine (0.725 g, 3.16 mmol), and (1R)-(−)-(10-camphorsulfonyl)oxaziridine (0.725 g, 3.16 mmol) were added to a solution of the synthesis intermediate obtained by the procedures described above in THF (50 mL), and the mixture was stirred at room temperature for 2 hours. To the reaction solution, a saturated ammonium chloride aqueous solution was added, followed by extraction with ethyl acetate. The obtained organic layer was washed with a saturated sodium bicarbonate aqueous solution and brine in this order and dried over anhydrous sodium sulfate, and the solvent was distilled off under reduced pressure. The obtained residue was purified by silica gel column chromatography [elute: dichloromethane/methanol=99/1-90/10 (gradient)] to obtain the title compound (2.77 g, yield: 84%).
$^1$H-NMR (400 MHz, DMSO-d$_6$) δ: 11.52 (1H, s), 7.38-7.17 (10H, m), 6.86 (1H, s), 4.12-3.89 (3H, m), 3.73 (3H, s), 2.89-2.67 (3H, m), 1.81-1.29 (4H, m), 1.39 (9H, s).

(3) tert-Butyl (+)-4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate

[Formula 9]

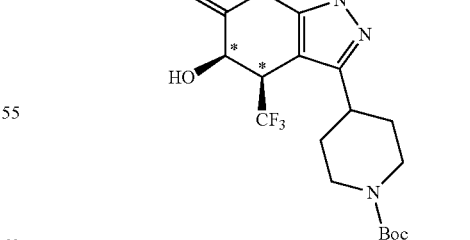

Lithium hydroxide monohydrate (0.873 g, 20.8 mmol) was added to a mixed solution of methyl 3-[1-(tert-butoxycarbonyl)piperidin-4-yl]-1-(diphenylmethyl)-5-hydroxy-6-oxo-4-(trifluoromethyl)-4,5,6,7-tetrahydro-1H-pyrazolo[3,4-b]pyridine-5-carboxylate (4.36 g, 6.94 mmol) produced in (2) in 1,4-dioxane (50 mL) and water (20 mL), and the mixture was stirred at 50° C. for 1 hour. The reaction solution was cooled to room temperature, and a saturated ammonium chloride aqueous solution was added thereto, followed by extraction with ethyl acetate. The obtained organic layer was washed with a saturated sodium bicarbonate aqueous solution and brine in this order and dried over anhydrous sodium sulfate, and the solvent was distilled off under reduced pressure. The obtained residue was purified by silica gel column chromatography [elute: hexane/ethyl acetate=95/5-50/50 (gradient)] to obtain a synthesis intermediate.

A portion (1.23 g) of the synthesis intermediate obtained by the procedures described above was dissolved in ethyl acetate. To the solution, a neutral silica gel was added for adsorption, and the solvent was distilled off under reduced pressure. The obtained powder was purified by flash LC [column: Chiralflash IC (30 mm i.d.×100 mm); manufactured by Daicel Corporation, elute: hexane/ethanol=91/9, flow rate: 12 mL/min] to obtain the title compound (0.55 g, yield: 27%, optically active form).

The optical purity was measured using HPLC [column: Chiralpak IA (4.6 mm i.d.×250 mm); manufactured by Daicel Corporation, elute: hexane/IPA=70/30, flow rate: 1.0 mL/min].

Optical purity: 99% or higher (retention time: 4.3 min);
$^1$H-NMR (400 MHz, DMSO-$d_6$) δ: 11.21 (1H, s), 7.37-7.15 (10H, m), 6.74 (1H, s), 5.79 (1H, d, J=4 Hz), 4.57-4.54 (1H, m), 4.16-3.90 (3H, m), 2.86-2.39 (3H, m), 1.83-1.35 (4H, m), 1.39 (9H, s);
$[\alpha]_D^{25}$=+35° (DMF, c=1.00).

(4) (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one

[Formula 10]

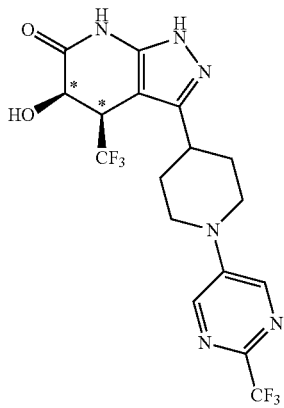

Chlorotrimethylsilane (0.31 mL, 2.5 mmol) and sodium iodide (0.31 g, 2.1 mmol) were added to a mixed solution of tert-butyl (+)-4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate (0.52 g, 0.91 mmol) produced in (3) in dichloromethane (25 mL) and acetonitrile (10 mL), and the mixture was stirred at room temperature for 2 hours. The solvent in the reaction solution was distilled off under reduced pressure, and the residue was separated into organic and aqueous layers by the addition of a saturated sodium bicarbonate aqueous solution and ethyl acetate. The obtained organic layer was washed with brine and dried over anhydrous sodium sulfate, and the solvent was distilled off under reduced pressure.

5-Chloro-2-(trifluoromethyl)pyrimidine (0.37 mL, 2.0 mmol) and DBU (0.62 mL, 4.2 mmol) were added to a solution of the obtained residue in DMSO (30 mL), and the mixture was stirred at 70° C. for 18 hours. The reaction solution was diluted with ethyl acetate, washed with water and brine in this order, and dried over anhydrous sodium sulfate, and the solvent was distilled off under reduced pressure. The obtained residue was purified by silica gel column chromatography [elute: hexane/ethyl acetate=95/5-50/50 (gradient)] to obtain a synthesis intermediate.

Triethylsilane (0.200 mL, 1.26 mmol) and trifluoroacetic acid (1.0 mL, 13 mmol) were added to a solution of the synthesis intermediate obtained by the procedures described above in dichloromethane (3 mL), and the mixture was stirred at room temperature for 1 hour. The solvent in the reaction solution was distilled off, and the residue was separated into organic and aqueous layers by the addition of ethyl acetate and a saturated sodium bicarbonate aqueous solution. The obtained organic layer was washed with brine and dried over anhydrous sodium sulfate, and the solvent was distilled off under reduced pressure. The obtained residue was purified by silica gel column chromatography [elute: ethyl acetate/methanol=50/50-0/100 (gradient)] to obtain the title compound (0.11 g, yield: 26%, optically active form).

$^1$H-NMR (400 MHz, DMSO-$d_6$) δ: 12.22 (1H, s), 10.55 (1H, s), 8.67 (2H, s), 5.53 (1H, d, J=3 Hz), 4.44 (1H, d, J=6 Hz), 4.25-4.10 (3H, m), 3.14-2.95 (3H, m), 1.93-1.38 (4H, m);
MS (ESI) m/z: 451 (M+H)$^+$:
$[\alpha]_D^{25}$=+7.2° (DMF, c=1.00).

(5) (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate Water (399 μl) was added to (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one (19.93 mg) produced in (4) at room temperature, and then, the mixture was stirred at 40° C. for approximately 20 hours and subsequently stirred at room temperature for approximately 0.5 hours. The solid was collected by filtration and then dried overnight at room temperature to obtain the title compound (17.63 mg). Rate of recovery: 85%.

Elemental analysis value in terms of $C_{17}H_{16}F_6N_6O_2 \cdot 1.0H_2O$
Calcd: C, 43.60; H, 3.87; F, 24.34; N, 17.94.
Found: C, 43.64; H, 3.87; F, 24.35; N, 17.68.

Table 6 shows peaks having a relative intensity of 20 or larger when the largest peak intensity in the diffraction pattern of powder X-ray diffraction (CuKα, λ=1.54 angstroms, scanning rate=20°/min) in FIG. 6 is defined as 100.

TABLE 6

| Peak No. | 2θ | d value | Relative intensity |
| --- | --- | --- | --- |
| 1 | 9.72 | 9.09 | 71 |
| 2 | 11.14 | 7.94 | 34 |
| 3 | 11.66 | 7.58 | 22 |
| 4 | 16.68 | 5.31 | 54 |
| 5 | 17.84 | 4.97 | 39 |

TABLE 6-continued

| Peak No. | 2θ | d value | Relative intensity |
|---|---|---|---|
| 6 | 18.94 | 4.68 | 29 |
| 7 | 19.26 | 4.60 | 68 |
| 8 | 19.70 | 4.50 | 100 |
| 9 | 23.00 | 3.86 | 20 |
| 10 | 25.42 | 3.50 | 94. |

(Example 7) (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate Toluene (407 μl) was added to (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one (20.37 mg) produced in Example 6(4) at room temperature, and then, the mixture was stirred at 40° C. for approximately 20 hours and subsequently stirred at room temperature for approximately 0.5 hours. The solid was collected by filtration and then dried overnight at room temperature to obtain the title compound (18.10 mg). Rate of recovery: 85%.

Elemental analysis value in terms of $C_{17}H_{16}F_6N_6O_2 \cdot 1.0H_2O \cdot 0.05C_7H_8$
Calcd: C, 44.06; H, 3.92; F, 24.10; N, 17.77.
Found: C, 44.27; H, 3.67; F, 24.37; N, 17.54.

Table 7 shows peaks having a relative intensity of 58 or larger when the largest peak intensity in the diffraction pattern of powder X-ray diffraction (CuKα, λ=1.54 angstroms, scanning rate=20°/min) in FIG. 7 is defined as 100.

TABLE 7

| Peak No. | 2θ | d value | Relative intensity |
|---|---|---|---|
| 1 | 3.68 | 23.99 | 86 |
| 2 | 14.86 | 5.96 | 58 |
| 3 | 16.86 | 5.25 | 59 |
| 4 | 17.06 | 5.19 | 64 |
| 5 | 17.48 | 5.07 | 68 |
| 6 | 17.94 | 4.94 | 90 |
| 7 | 18.94 | 4.68 | 67 |
| 8 | 19.36 | 4.58 | 77 |
| 9 | 19.62 | 4.52 | 62 |
| 10 | 20.18 | 4.40 | 100. |

(Example 8) (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one Toluene (402 μl) was added to (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one (20.08 mg) produced in Example 6(4) at room temperature, and then, the mixture was stirred at 60° C. for approximately 20 hours and subsequently stirred at room temperature for approximately 0.5 hours. The solid was collected by filtration and then dried overnight at room temperature to obtain the title compound (16.13 mg). Rate of recovery: 80%.

Elemental analysis value in terms of $C_{17}H_{16}F_6N_6O_2$
Calcd: C, 45.34; H, 3.58; F, 25.31; N, 18.66.
Found: C, 45.45; H, 3.61; F, 25.27; N, 18.28.

Table 8 shows peaks having a relative intensity of 4 or larger when the largest peak intensity in the diffraction pattern of powder X-ray diffraction (CuKα, λ=1.54 angstroms, scanning rate=20°/min) in FIG. 8 is defined as 100.

TABLE 8

| Peak No. | 2θ | d value | Relative intensity |
|---|---|---|---|
| 1 | 5.66 | 15.60 | 100 |
| 2 | 9.54 | 9.26 | 4 |
| 3 | 12.38 | 7.14 | 12 |
| 4 | 17.00 | 5.21 | 69 |
| 5 | 21.82 | 4.07 | 15 |
| 6 | 22.90 | 3.88 | 4 |
| 7 | 26.12 | 3.41 | 4 |
| 8 | 27.50 | 3.24 | 10 |
| 9 | 28.72 | 3.11 | 4 |
| 10 | 33.10 | 2.70 | 9. |

(Example 9) (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one (20.58 mg) produced in Example 6(4) was treated by heating to 280° C. in a thermal analysis apparatus, and then, toluene (412 μl) was added thereto at room temperature. Then, the mixture was stirred at 10° C. for approximately 20 hours and subsequently stirred at room temperature for approximately 0.5 hours. The solid was collected by filtration and then dried overnight at room temperature to obtain the title compound (17.95 mg). Rate of recovery: 87%.

Elemental analysis value in terms of $C_{17}H_{16}F_6N_6O_2$
Calcd: C, 45.34; H, 3.58; F, 25.31; N, 18.66.
Found: C, 45.18; H, 3.50; F, 25.46; N, 18.38.

Table 9 shows peaks having a relative intensity of 30 or larger when the largest peak intensity in the diffraction pattern of powder X-ray diffraction (CuKα, λ=1.54 angstroms, scanning rate=20°/min) in FIG. 9 is defined as 100.

TABLE 9

| Peak No. | 2θ | d value | Relative intensity |
|---|---|---|---|
| 1 | 8.94 | 9.88 | 72 |
| 2 | 14.48 | 6.11 | 62 |
| 3 | 15.86 | 5.58 | 74 |
| 4 | 17.42 | 5.09 | 30 |
| 5 | 17.70 | 5.01 | 34 |
| 6 | 18.00 | 4.92 | 93 |
| 7 | 20.38 | 4.35 | 100 |
| 8 | 23.20 | 3.83 | 38 |
| 9 | 23.64 | 3.76 | 57 |
| 10 | 27.16 | 3.28 | 31. |

(Example 10) (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one produced in Example 6(4) was treated by heating to 280° C. in a thermal analysis apparatus. To the resulting specimen (57.12 mg), nitromethane (571 µl) was added at room temperature. Then, the mixture was stirred at 10° C. for approximately 4 hours and subsequently stirred at room temperature for approximately 1.5 hours. The solid was collected by filtration and then dried overnight at room temperature to obtain the title compound (27.81 mg). Rate of recovery: 49%.

Elemental analysis value in terms of $C_{17}H_{16}F_6N_6O_2 \cdot 0.75H_2O \cdot 0.05C_7H_3NO_2$
Calcd: C, 43.86; H, 3.81; F, 24.41; N, 18.15.
Found: C, 43.59; H, 3.57; F, 24.65; N, 18.28.

Table 10 shows peaks having a relative intensity of 23 or larger when the largest peak intensity in the diffraction pattern of powder X-ray diffraction (CuKα, λ=1.54 angstroms, scanning rate=20°/min) in FIG. 10 is defined as 100.

TABLE 10

| Peak No. | 2θ | d value | Relative intensity |
|---|---|---|---|
| 1 | 10.66 | 8.29 | 26 |
| 2 | 14.96 | 5.92 | 83 |
| 3 | 16.06 | 5.51 | 51 |
| 4 | 16.70 | 5.30 | 38 |
| 5 | 18.64 | 4.76 | 27 |
| 6 | 19.70 | 4.50 | 100 |
| 7 | 20.84 | 4.26 | 48 |
| 8 | 22.30 | 3.98 | 23 |
| 9 | 23.34 | 3.81 | 23 |
| 10 | 24.28 | 3.66 | 38. |

(Example 11) (+)-cis-5R-Hydroxy-4R-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one (20.07 mg) produced in Example 6(4) was completely dissolved by the addition of acetone (200 µl). Then, acetone was distilled off in a centrifugal concentrator, and n-butyl acetate (200 µl) was added to the residue. Then, the mixture was stirred at 40° C. for approximately 4 hours and at room temperature for approximately 0.5 hours, and the precipitated solid was collected by filtration and then dried overnight at room temperature to obtain the title compound (14.43 mg). Rate of recovery: 72%.

Elemental analysis value in terms of $C_{17}H_{16}F_6N_6O_2$
Calcd: C, 45.34; H, 3.58; F, 25.31; N, 18.66.
Found: C, 45.27; H, 3.46; F, 25.47; N, 18.40.

Table 11 shows peaks having a relative intensity of 11 or larger when the largest peak intensity in the diffraction pattern of powder X-ray diffraction (CuKα, λ=1.54 angstroms, scanning rate=20°/min) in FIG. 11 is defined as 100.

TABLE 11

| Peak No. | 2θ | d value | Relative intensity |
|---|---|---|---|
| 1 | 7.36 | 12.00 | 18 |
| 2 | 10.36 | 8.53 | 31 |
| 3 | 14.52 | 6.10 | 15 |
| 4 | 16.34 | 5.42 | 100 |
| 5 | 19.46 | 4.56 | 46 |
| 6 | 20.52 | 4.32 | 11 |
| 7 | 23.20 | 3.83 | 59 |
| 8 | 24.70 | 3.60 | 29 |
| 9 | 26.24 | 3.39 | 13 |
| 10 | 29.38 | 3.04 | 15. |

(Example 12) (+)-cis-5R-Hydroxy-4R-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate 60% aqueous ethanol (200 µl) was added to (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one (20.23 mg) produced in Example 6(4), and the mixture was stirred at 25° C. for approximately 24 hours and at room temperature for approximately 0.5 hours. The precipitated solid was collected by filtration and then dried overnight at room temperature to obtain the title compound (19.20 mg). Rate of recovery: 82%.

Elemental analysis value in terms of $C_{17}H_{16}F_6N_6O_2 \cdot 4.2H_2O$
Calcd: C, 38.82; H, 4.68; F, 21.67; N, 15.98.
Found: C, 38.62; H, 4.56; F, 21.90; N, 15.82.

Table 12 shows peaks having a relative intensity of 28 or larger when the largest peak intensity in the diffraction pattern of powder X-ray diffraction (CuKα, λ=1.54 angstroms, scanning rate=20°/min) in FIG. 12 is defined as 100.

TABLE 12

| Peak No. | 2θ | d value | Relative intensity |
|---|---|---|---|
| 1 | 8.32 | 10.62 | 100 |
| 2 | 9.90 | 8.93 | 91 |
| 3 | 10.70 | 8.26 | 45 |
| 4 | 16.66 | 5.32 | 29 |
| 5 | 16.68 | 5.25 | 28 |
| 6 | 17.88 | 4.96 | 35 |
| 7 | 19.36 | 4.58 | 43 |
| 8 | 19.62 | 4.52 | 62 |
| 9 | 19.96 | 4.44 | 79 |
| 10 | 23.16 | 3.84 | 30. |

(Test Example 1) LCAT Activity Measurement (In Vitro)

A fraction composed of HDL3 (1.125<specific gravity <1.210 g/mL) was obtained from the plasma of a healthy person by density gradient centrifugation. The obtained fraction was dialyzed against phosphate-buffered saline (pH 7.4) and used as an enzyme source and an acceptor for LCAT. Each test drug was prepared by dissolution in dimethyl sulfoxide. [$^{14}$C]Cholesterol containing DTNB (Ellman's reagent, final concentration: 0.5 mM), mercaptoethanol (final concentration: 12.5 mM), and 0.6% bovine serum albumin was added to phosphate-buffered saline (pH 7.4) containing 1 mg/mL HDL3, and the test drug was further added thereto at varying concentrations to adjust the whole amount to 80 µL. This mixture was incubated at 37° C. for approximately 16 hours. Then, a mixed solution of hexane and isopropanol (mixing ratio=3:2) was added thereto to stop the reaction. After stirring, the hexane layer was collected, and this layer was evaporated to dryness. A chloroform solution (concentration: 10 mg/mL) was added thereto, and the mixture was spotted onto a thin-layer silica gel plate and developed using a mixed solution of hexane, diethyl ether, and ethyl acetate (mixing ratio=85:15:2). The radioactivity of a portion corresponding to cholesterol oleate was measured using an imaging analyzer BAS-2500 (manufactured by Fujifilm Corp.). A sample non-supplemented with the test drug was similarly treated and assayed. The $EC_{50}$ value of LCAT activation was calculated according to the expression given below relative to the LCAT activity in the sample non-supplemented with the test drug. The results are shown in Table 13.

$$Y = \text{Bottom} + \frac{(\text{Top} - \text{Bottom})}{1 + 10^{LogEC50-X}} \quad \text{[Expression 1]}$$

wherein X represents the logarithm of the concentration of the test drug;

Y represents the responsiveness (LCAT activity) of the test drug;

Top represents the maximum value (maximum plateau);

Bottom represents the minimum value (minimum plateau); and $EC_{50}$ represents the 50% effective concentration.

TABLE 13

| Test compound | $EC_{50}(\mu M)$ |
|---|---|
| Compound of Example 1(4) | 0.004 |
| Compound of Example 6(4) | 0.018 |

As seen from these results, the compound of the present invention has an excellent LCAT-activating effect and is useful as a medicament for the treatment or prophylaxis of diseases such as dyslipidemia and arteriosclerosis.

(Test Example 2) LCAT Activity Measurement (Plasma)

The plasma of a human, a cynomolgus monkey, or a human LCAT transgenic mouse is used as an enzyme source and an acceptor for LCAT. Each test drug is prepared by dissolution in dimethyl sulfoxide. [14C]Cholesterol containing DTNB (Ellman's reagent, final concentration: 0.5 mM), mercaptoethanol (final concentration: 12.5 mM), and 0.6% bovine serum albumin is added to 5 µL of each plasma and 45 µL of PBS, and the test drug is further added thereto at varying concentrations to adjust the whole amount to 80 µL. This mixture is incubated at 37° C. for approximately 16 hours. Then, a mixed solution of hexane and isopropanol (mixing ratio=3:2) is added thereto to stop the reaction. After addition of water and stirring, the hexane layer is collected, and this layer is evaporated to dryness. A chloroform solution (concentration: 10 mg/mL) is added thereto, and the mixture is spotted onto a thin-layer silica gel plate and developed using a mixed solution of hexane, diethyl ether, and ethyl acetate (mixing ratio=85:15:2). The radioactivity of a portion corresponding to cholesterol oleate is measured using an imaging analyzer BAS-2500 (manufactured by Fujifilm Corp.). A sample non-supplemented with the test drug is similarly treated and assayed. The $EC_{50}$ value of LCAT activation is calculated according to the expression given below relative to the LCAT activity in the sample non-supplemented with the test drug.

$$Y = \text{Bottom} + \frac{(\text{Top} - \text{Bottom})}{1 + 10^{LogEC50-X}} \quad \text{[Expression 2]}$$

wherein X represents the logarithm of the concentration of the test drug;

Y represents the responsiveness (LCAT activity) of the test drug;

Top represents the maximum value (maximum plateau);

Bottom represents the minimum value (minimum plateau); and $EC_{50}$ represents the 50% effective concentration.

(Test Example 3) LCAT Activity Measurement (Ex Vivo)

LCAT activity in the plasma of a cynomolgus monkey or a human LCAT transgenic mouse receiving each test drug is measured. [14C]Cholesterol containing DTNB (Ellman's reagent, final concentration: 0.26 mM), mercaptoethanol (final concentration: 2 mM), and 0.6% bovine serum albumin is added to 25 µL of each plasma to adjust the whole amount to 40 µL. This mixture is incubated at 37° C. for 1 hour. Then, a mixed solution of hexane and isopropanol (mixing ratio=3:2) is added thereto to stop the reaction. After addition of water and stirring, the hexane layer is collected, and this layer is evaporated to dryness. A chloroform solution (concentration: 10 mg/mL) is added thereto, and the mixture is spotted onto a thin-layer silica gel plate and developed using a mixed solution of hexane, diethyl ether, and ethyl acetate (mixing ratio=85:15:2). The radioactivity of a portion corresponding to cholesterol oleate is measured using an imaging analyzer BAS-2500 (manufactured by Fujifilm Corp.). The rate of change in LCAT activation at each point in time compared with the LCAT activity before administration is calculated.

(Test Example 4) Drug Efficacy Test in Cynomolgus Monkeys

Each test drug was dissolved in a propylene glycol (Sigma-Aldrich Corp.)-Tween 80 (Sigma-Aldrich Corp.) mixed solution [4/1 (v/v)] or a 0.5% (w/v) methylcellulose aqueous solution, and the solution was orally administered to a cynomolgus monkey for 1 or 7 days. At 1 or 7 day of administration period, blood was collected before administration and after administration, and plasma was obtained. The content of cholesterol in the plasma was measured using a commercially available assay kit (Cholesterol-E Wako, Wako Pure Chemical Industries, Ltd.). The lipoprotein profile was analyzed by HPLC (column: LipopropakXL, manufactured by Tosoh Corp.). The contents of HDL cholesterol and non-HDL cholesterol were calculated according to the following calculation expression:

Content of HDL cholesterol=Content of cholesterol in the plasma×(Peak area of HDL cholesterol/Total sum of peaks)

Content of non-HDL cholesterol=Content of cholesterol in the plasma×(Peak area of non-HDL cholesterol/Total sum of peaks)

The rate (%) of increase in HDL level after the administration of a single dose of 10 mg/kg compared with before administration was determined from the AUC before administration and 24 hours after administration. The results are shown in Table 14.

TABLE 14

| Test compound | Rate of increase in HDL level after administration of single dose |
|---|---|
| Compound of Example 1(4) | 590 |
| Compound of Example 6(4) | 483 |

(Test Example 5) Drug Efficacy Test in Human LCAT Transgenic Mice

Each test drug is dissolved in a propylene glycol-Tween 80 mixed solution [4/1 (v/v)] or a 0.5% (w/v) methylcellulose aqueous solution, and the solution is orally administered to a human LCAT transgenic mouse for 1, 4, or 7 days. At 1, 4, or 7 day of administration period, blood is collected before administration and after administration, and plasma is obtained. The content of cholesterol in the plasma is measured using a commercially available assay kit (Cholesterol-E Wako, Wako Pure Chemical Industries, Ltd.). The lipoprotein profile is analyzed by HPLC (column: LipopropakXL, manufactured by Tosoh Corp.). The contents of HDL cholesterol and non-HDL cholesterol are calculated according to the following calculation expression:

Content of HDL cholesterol=Content of cholesterol in the plasma×(Peak area of HDL cholesterol/ Total sum of peaks)

Content of non-HDL cholesterol=Content of cholesterol in the plasma×(Peak area of non-HDL cholesterol/Total sum of peaks)

As seen from these results, the compound of the present invention exhibits an excellent LCAT-activating effect and is useful as a medicament for the treatment or prophylaxis of diseases such as dyslipidemia and arteriosclerosis.

(Formulation Example 1) Hard Capsule

Each standard two-piece hard gelatin capsule shell is filled with 100 mg of the compound of Example 1 in a powder form, 150 mg of lactose, 50 mg of cellulose, and 6 mg of magnesium stearate to produce a unit capsule, which is in turn washed and then dried.

(Formulation Example 2) Soft Capsule

A mixture of the compound of Example 2 put in a digestible oil, for example, soybean oil, cottonseed oil, or olive oil, is prepared and injected into a gelatin shell using a positive displacement pump to obtain a soft capsule containing 100 mg of the active ingredient, which is in turn washed and then dried.

(Formulation Example 3) Tablet

According to a routine method, a tablet is produced using 100 mg of the compound of Example 3, 0.2 mg of colloidal silicon dioxide, 5 mg of magnesium stearate, 275 mg of microcrystalline cellulose, 11 mg of starch, and 98.8 mg of lactose.

If desired, the tablet is coated.

(Formulation Example 4) Suspension

A suspension is produced to contain 100 mg of the compound of Example 4 pulverized into a fine powder, 100 mg of sodium carboxy methylcellulose, 5 mg of sodium benzoate, 1.0 g of a sorbitol solution (Japanese Pharmacopoeia), and 0.025 mL of vanillin in 5 mL.

(Formulation Example 5) Injection

The compound of Example 6 (1.5% by weight) is stirred in 10% by weight of propylene glycol, subsequently adjusted to a fixed volume with injectable water, and then sterilized to prepare an injection.

INDUSTRIAL APPLICABILITY

The compound represented by the general formula (I) of the present invention or the pharmacologically acceptable salt thereof has an excellent LCAT-activating effect and is particularly useful as an active ingredient in a therapeutic or prophylactic agent for arteriosclerosis, arteriosclerotic heart disease, coronary heart disease (including acute coronary syndromes, heart failure, myocardial infarction, angina pectoris, cardiac ischemia, cardiovascular disturbance, and restenosis caused by angiogenesis), cerebrovascular disease (including stroke and cerebral infarction), peripheral vascular disease (including peripheral arterial disease and diabetic vascular complications), dyslipidemia, LCAT deficiency, hypo-HDL-cholesterolemia, hyper-LDL-cholesterolemia, diabetes mellitus, hypertension, metabolic syndrome, Alzheimer's disease, cornea opacity, or renal disease, particularly, an anti-arteriosclerotic agent.

The invention claimed is:

1. A crystal of a compound represented by formula (I) or a pharmacologically acceptable salt thereof:

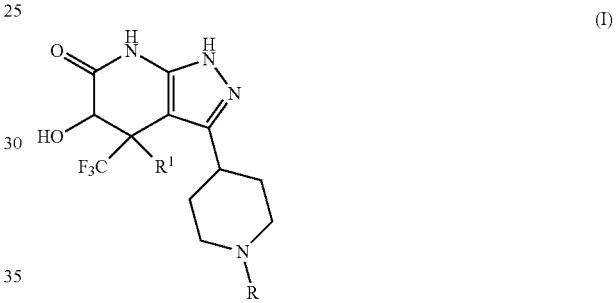

(I)

wherein $R^1$ represents a hydrogen atom or a hydroxy group, and R represents a 2-(trifluoromethyl)pyrimidin-5-yl group or a 5-(trifluoromethyl)pyrazin-2-yl group.

2. The crystal according to claim 1, wherein $R^1$ is a hydrogen atom, and R is a 2-(trifluoromethyl)pyrimidin-5-yl group.

3. The crystal according to claim 1, wherein $R^1$ is a hydroxy group, and R is a 5-(trifluoromethyl)pyrazin-2-yl group.

4. A crystal according to claim 1, wherein the crystal is a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one or (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one, or a hydrate thereof.

5. A crystal according to claim 1, wherein the crystal is a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate which exhibits main peaks at d-spacings of 8.86, 7.19, 6.67, 6.07, 5.51, 4.76, 4.61, 3.94, 3.79, and 3.47 angstroms in a powder X-ray diffraction pattern obtained by exposure to copper Kα radiation.

6. A crystal according to claim 1, wherein the crystal is a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate which exhibits main peaks at d-spacings of 15.28, 7.70, 6.67, 6.17, 5.62, 5.01, 4.58, 4.43, 3.77, and 3.30 angstroms in a powder X-ray diffraction pattern obtained by exposure to copper Kα radiation.

7. A crystal according to claim 1, wherein the crystal is a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate which exhibits main peaks at d-spacings of 14.97, 11.50, 9.84, 9.50, 7.12, 5.73, 5.48, 4.95, 4.46, and 3.81 angstroms in a powder X-ray diffraction pattern obtained by exposure to copper Kα radiation.

8. A crystal according to claim 1, wherein the crystal is a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one hydrate which exhibits main peaks at d-spacings of 9.28, 7.28, 6.16, 5.96, 4.99, 4.86, 4.73, 4.53, 3.48, and 3.04 angstroms in a powder X-ray diffraction pattern obtained by exposure to copper Kα radiation.

9. A crystal according to claim 1, wherein the crystal is a crystal of (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one which exhibits main peaks at d-spacings of 18.79, 6.90, 6.21, 5.68, 5.56, 4.79, 4.56, 4.44, 3.76, and 3.44 angstroms in a powder X-ray diffraction pattern obtained by exposure to copper Kα radiation.

10. A crystal according to claim 1, wherein the crystal is a crystal of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate which exhibits main peaks at d-spacings of 9.09, 7.94, 7.58, 5.31, 4.97, 4.68, 4.60, 4.50, 3.86, and 3.50 angstroms in a powder X-ray diffraction pattern obtained by exposure to copper Kα radiation.

11. A crystal according to claim 1, wherein the crystal is a crystal of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate which exhibits main peaks at d-spacings of 23.99, 5.96, 5.25, 5.19, 5.07, 4.94, 4.68, 4.58, 4.52, and 4.40 angstroms in a powder X-ray diffraction pattern obtained by exposure to copper Kα radiation.

12. A crystal according to claim 1, wherein the crystal is a crystal of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one which exhibits main peaks at d-spacings of 15.60, 9.26, 7.14, 5.21, 4.07, 3.88, 3.41, 3.24, 3.11, and 2.70 angstroms in a powder X-ray diffraction pattern obtained by exposure to copper Kα radiation.

13. A crystal according to claim 1, wherein the crystal is a crystal of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one which exhibits main peaks at d-spacings of 9.88, 6.11, 5.58, 5.09, 5.01, 4.92, 4.35, 3.83, 3.76, and 3.28 angstroms in a powder X-ray diffraction pattern obtained by exposure to copper Kα radiation.

14. A crystal according to claim 1, wherein the crystal is a crystal of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one which exhibits main peaks at d-spacings of 8.29, 5.92, 5.51, 5.30, 4.76, 4.50, 4.26, 3.98, 3.81, and 3.66 angstroms in a powder X-ray diffraction pattern obtained by exposure to copper Kα radiation.

15. A crystal according to claim 1, wherein the crystal is a crystal of (+)-cis-5R-hydroxy-4R-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one which exhibits main peaks at d-spacings of 12.00, 8.53, 6.10, 5.42, 4.56, 4.32, 3.83, 3.60, 3.39, and 3.04 angstroms in a powder X-ray diffraction pattern obtained by exposure to copper Kα radiation.

16. A crystal according to claim 1, wherein the crystal is a crystal of (+)-cis-5R-hydroxy-4R-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one hydrate which exhibits main peaks at d-spacings of 10.62, 8.93, 8.26, 5.32, 5.25, 4.96, 4.58, 4.52, 4.44, and 3.84 angstroms in a powder X-ray diffraction pattern obtained by exposure to copper Kα radiation.

17. A pharmaceutical composition comprising a crystal according to claim 1 as an active ingredient.

18. A pharmaceutical composition comprising a crystal according to claim 17 further comprising a pharmacologically acceptable carrier.

19. A method for activating LCAT, comprising administering an effective amount of a crystal according to claim 1 to a human.

20. A method for treatment or prophylaxis of a disease, comprising administering an effective amount of a crystal according to claim 1 to a human wherein the disease is arteriosclerosis, arteriosclerotic heart disease, coronary heart disease, cerebrovascular disease, peripheral vascular disease, dyslipidemia, hypo-HDL-cholesterolemia, renal disease, or LCAT deficiency.

21. The method according to claim 20, wherein the disease is arteriosclerosis.

22. The method according to claim 20, wherein the disease is dyslipidemia.

23. The method according to claim 20, wherein the disease is a disease caused by an increased concentration of LDL cholesterol in the blood.

24. The method according to claim 20, wherein the disease is a disease caused by a decreased concentration of HDL cholesterol in the blood.

* * * * *